(12) United States Patent
Jackson et al.

(10) Patent No.: US 12,251,136 B2
(45) Date of Patent: *Mar. 18, 2025

(54) MEDICAL IMPLANT THREAD PLUG HAVING A LOWER ROD ENGAGING EXTENSION

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 104 days.

This patent is subject to a terminal disclaimer.

(21) Appl. No.: 18/188,855

(22) Filed: Mar. 23, 2023

(65) Prior Publication Data

US 2023/0225767 A1    Jul. 20, 2023

Related U.S. Application Data

(63) Continuation of application No. 17/808,438, filed on Jun. 23, 2022, now Pat. No. 11,911,075, which is a
(Continued)

(51) Int. Cl.
*A61B 17/70* (2006.01)
*A61B 17/86* (2006.01)
(Continued)

(52) U.S. Cl.
CPC ...... *A61B 17/7035* (2013.01); *A61B 17/7032* (2013.01); *A61B 17/863* (2013.01);
(Continued)

(58) Field of Classification Search
CPC ............ A61B 17/7035; A61B 17/7032; A61B 17/863; A61B 17/8665; A61B 17/8685; A61B 2090/037; A61B 2017/8655
(Continued)

(56) References Cited

U.S. PATENT DOCUMENTS

| 2003/0100896 A1* | 5/2003 | Biedermann | A61B 17/7049 606/305 |
| 2004/0039383 A1* | 2/2004 | Jackson | A61B 17/7091 606/273 |

(Continued)

*Primary Examiner* — Tessa M Matthews
*Assistant Examiner* — David C Comstock
(74) *Attorney, Agent, or Firm* — Polsinelli PC

(57) ABSTRACT

A receiver assembly for securing an elongate rod to a bone anchor including a receiver and a threaded plug. The receiver including an upper portion defining a channel to receive the elongate rod, an interior surface having helically wound receiver thread, and an exterior surface having in some embodiments first and second horizontal curvate extending instrument engaging grooves. The threaded plug including a longitudinal axis, a lower surface having a protrusion, and an external side surface having a continuous helically wound closure thread to rotatably mate with the helically wound receiver thread. The continuous helically wound closure thread including a lower leading surface and an upper trailing surface, both in some embodiments extending perpendicular to the longitudinal axis, and a cylindrical outer crest surface extending parallel to the longitudinal axis. When the protrusion on the threaded plug engages the elongate rod, the threaded plug does not extend overtop a top surface of the receiver.

10 Claims, 19 Drawing Sheets

Related U.S. Application Data continuation of application No. 17/476,652, filed on Sep. 16, 2021, now Pat. No. 11,399,873, which is a continuation of application No. 17/123,499, filed on Dec. 16, 2020, now Pat. No. 11,129,646, which is a continuation of application No. 16/779,304, filed on Jan. 31, 2020, now Pat. No. 10,898,233, which is a continuation of application No. 15/964,502, filed on Apr. 27, 2018, now Pat. No. 10,548,641, which is a continuation of application No. 15/469,076, filed on Mar. 24, 2017, now Pat. No. 9,956,004, which is a continuation of application No. 14/566,356, filed on Dec. 10, 2014, now Pat. No. 9,636,146, which is a continuation of application No. 13/694,849, filed on Jan. 10, 2013, now Pat. No. 8,911,479.

(60) Provisional application No. 61/634,361, filed on Feb. 28, 2012, provisional application No. 61/631,746, filed on Jan. 10, 2012.

(51) Int. Cl.
*A61B 17/88* (2006.01)
*A61B 90/00* (2016.01)

(52) U.S. Cl.
CPC ...... *A61B 17/8665* (2013.01); *A61B 17/8685* (2013.01); *A61B 2017/8655* (2013.01); *A61B 2090/037* (2016.02)

(58) Field of Classification Search
USPC ........ 606/246, 265, 266, 267, 270, 273, 306
See application file for complete search history.

(56) References Cited

U.S. PATENT DOCUMENTS

| | | | | |
|---|---|---|---|---|
| 2007/0208344 | A1* | 9/2007 | Young | A61B 17/7032 623/17.16 |
| 2008/0319490 | A1* | 12/2008 | Jackson | A61B 17/7008 606/301 |
| 2009/0138052 | A1* | 5/2009 | Biedermann | A61B 17/7037 606/264 |
| 2010/0125302 | A1* | 5/2010 | Hammill, Sr | A61B 17/7035 606/301 |
| 2010/0298891 | A1* | 11/2010 | Jackson | A61B 17/7008 606/305 |
| 2011/0270321 | A1* | 11/2011 | Prevost | A61B 17/7037 606/305 |

* cited by examiner

Fig. 18.
Fig. 19.
Fig. 20.
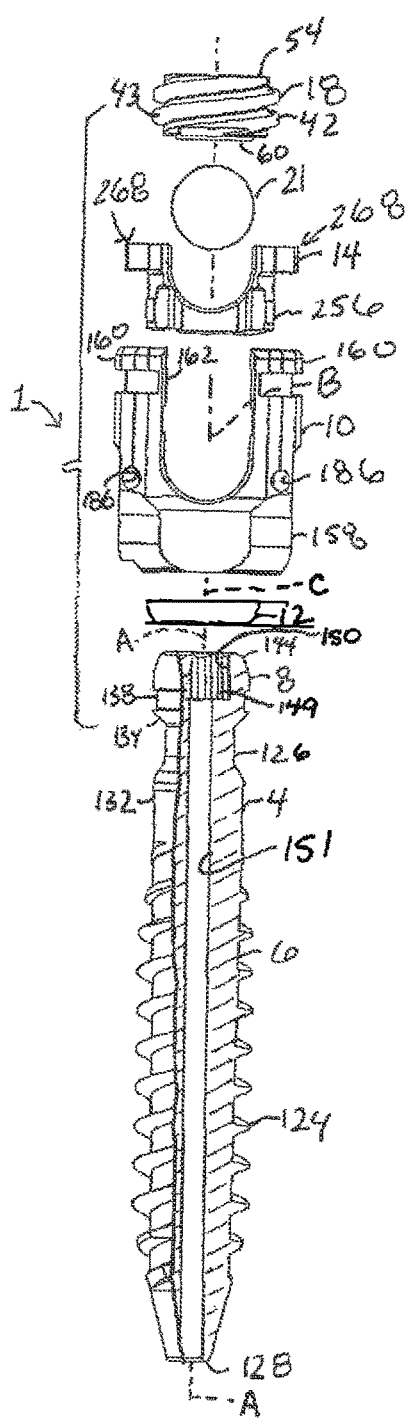
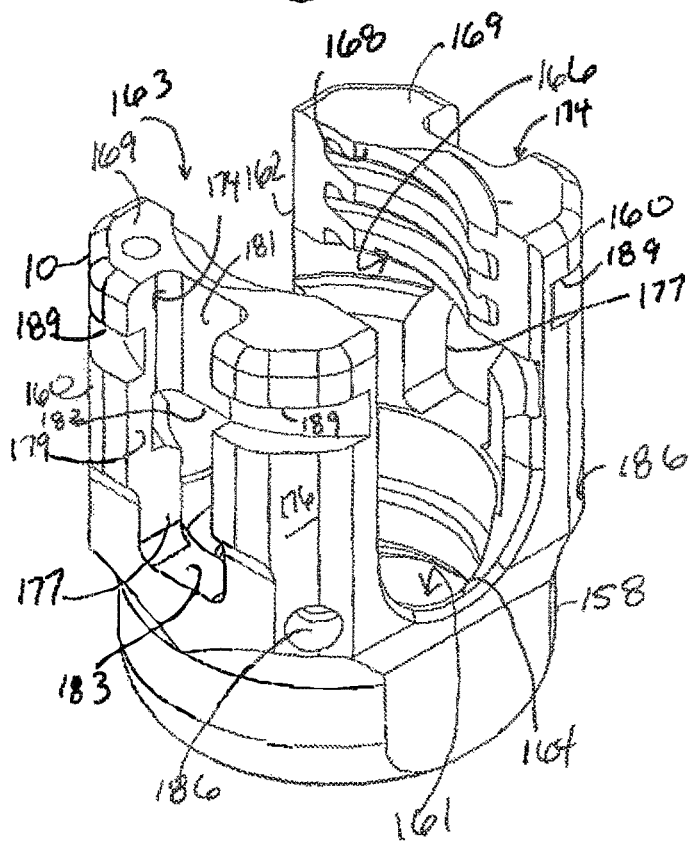
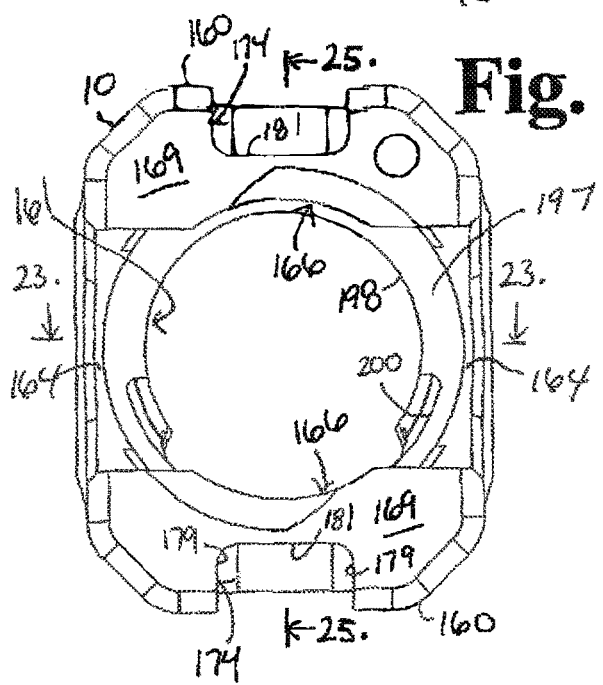

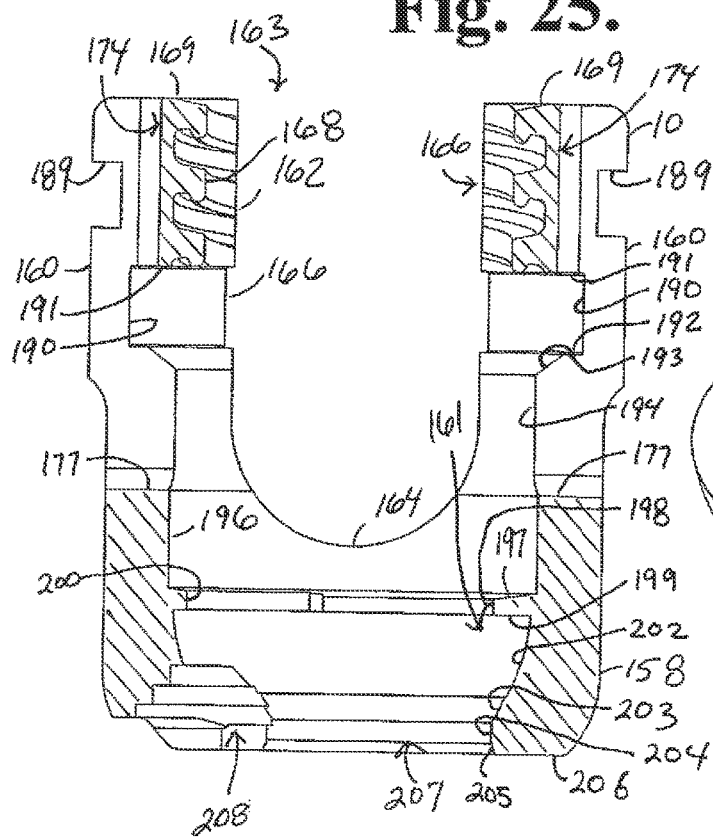
Fig. 25.
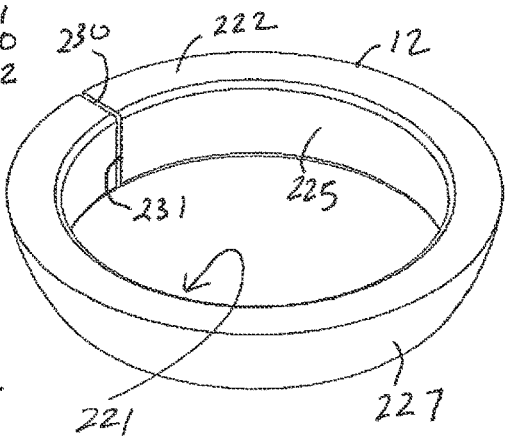
Fig. 26.
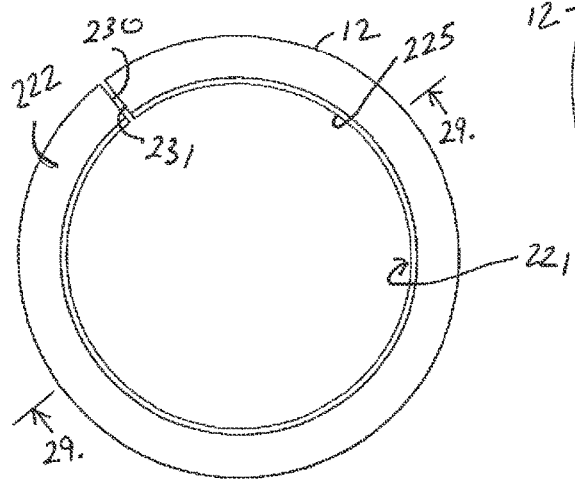
Fig. 27.
Fig. 28.

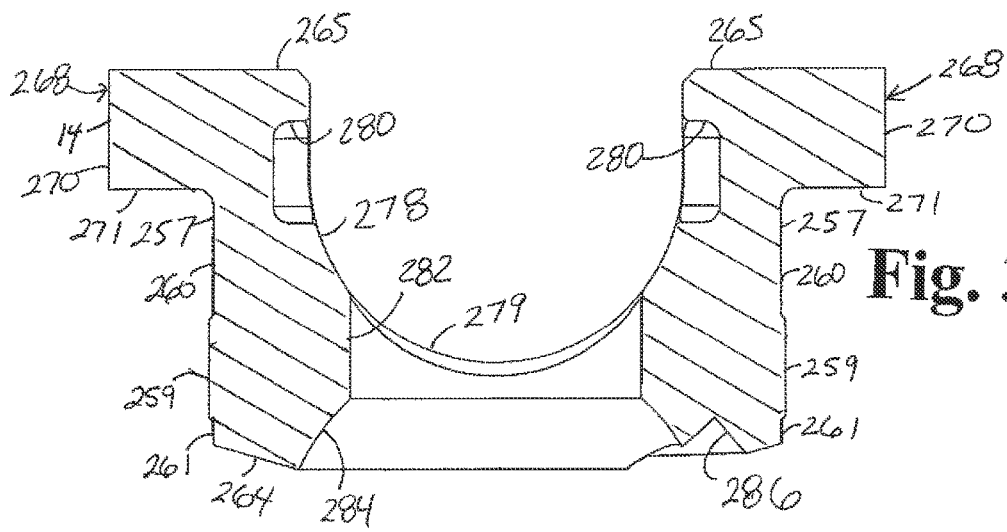
Fig. 36.
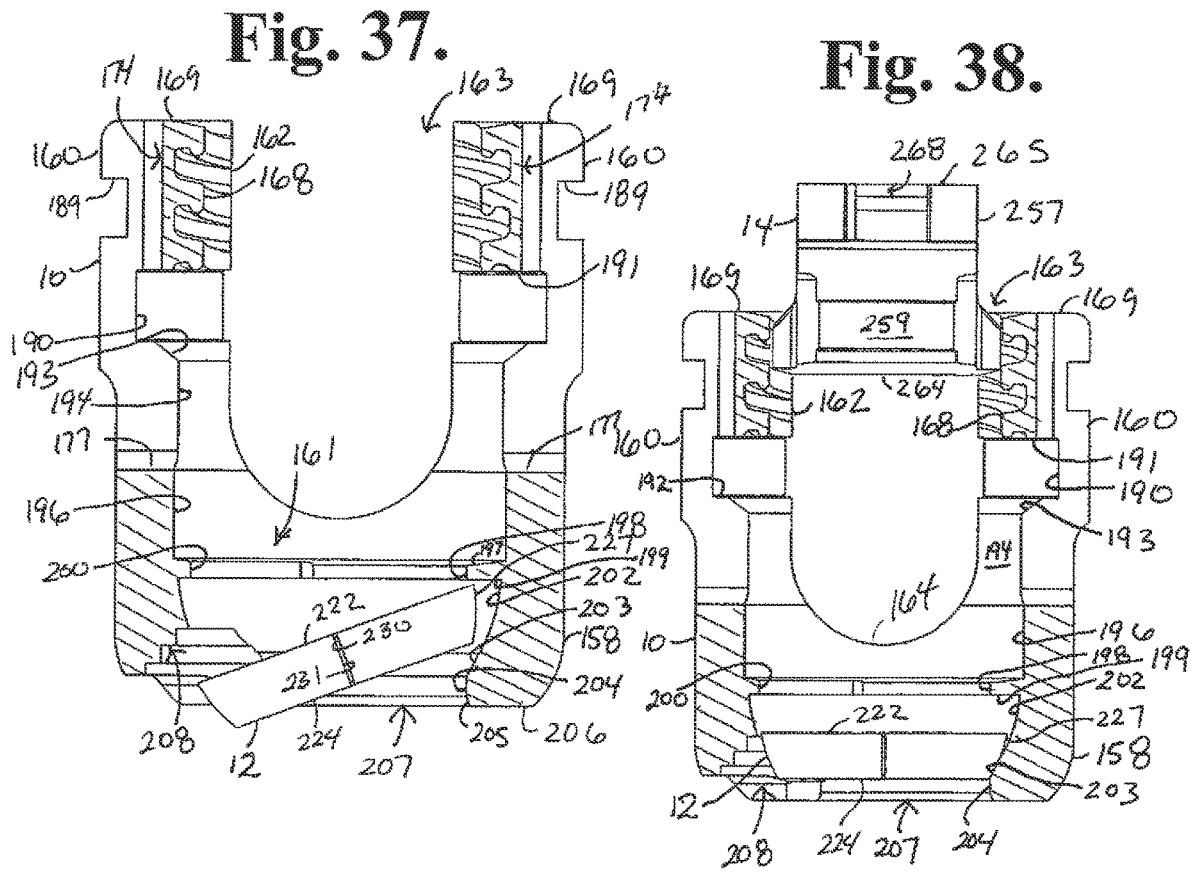
Fig. 37.
Fig. 38.

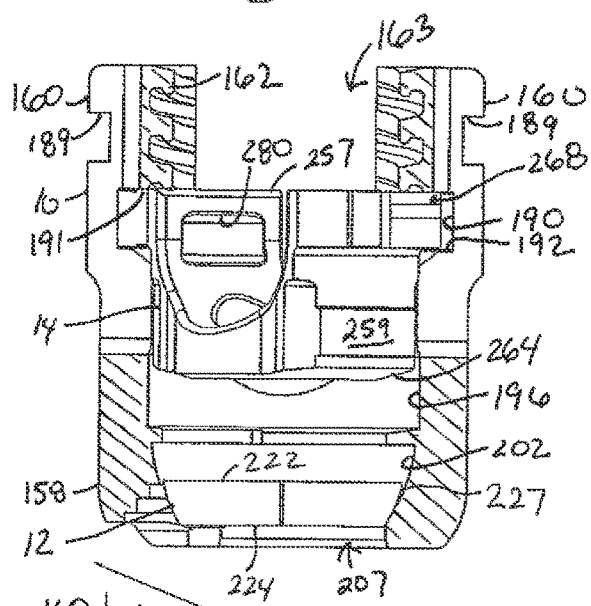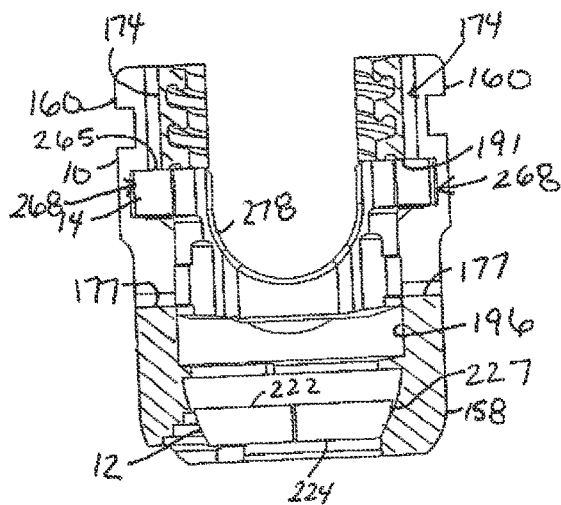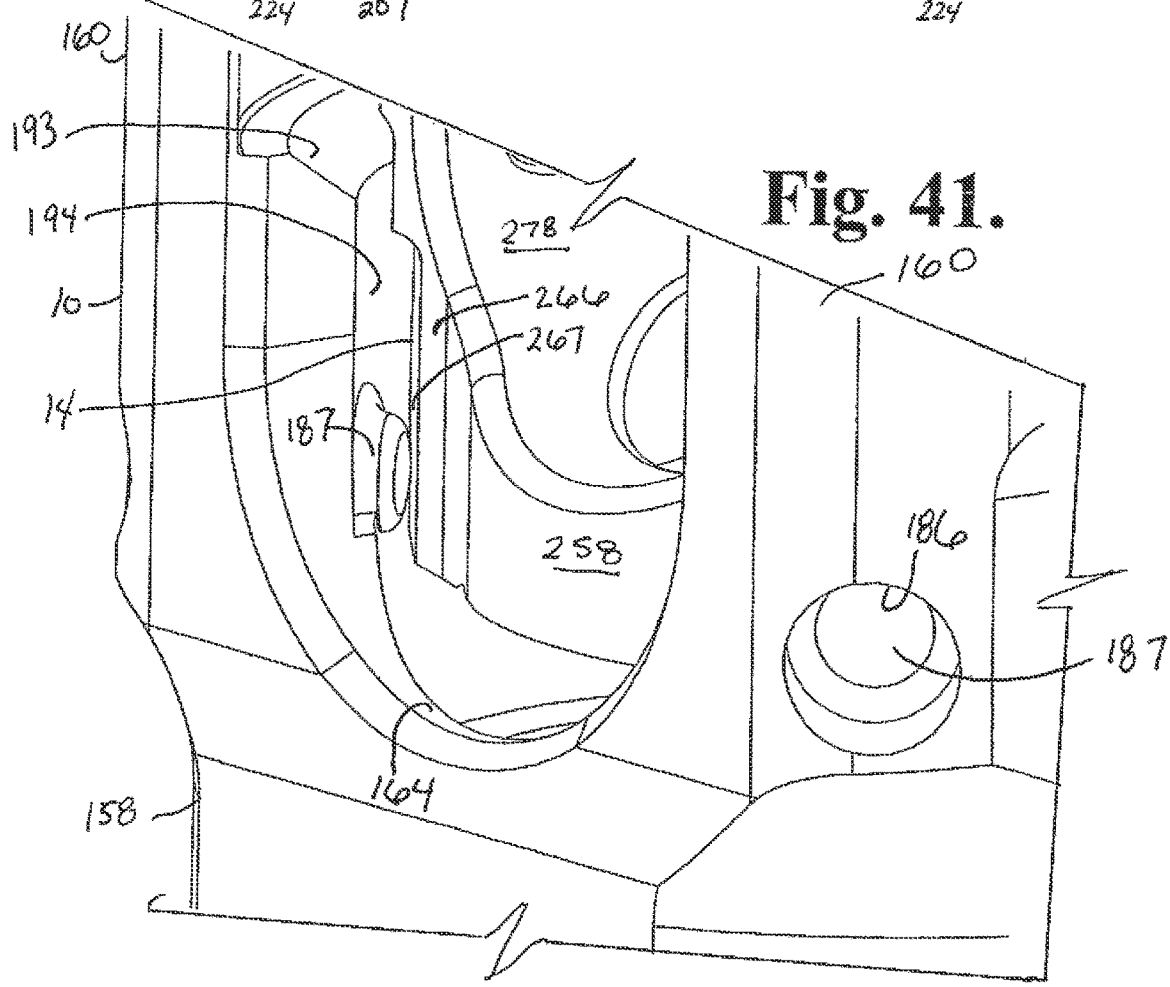

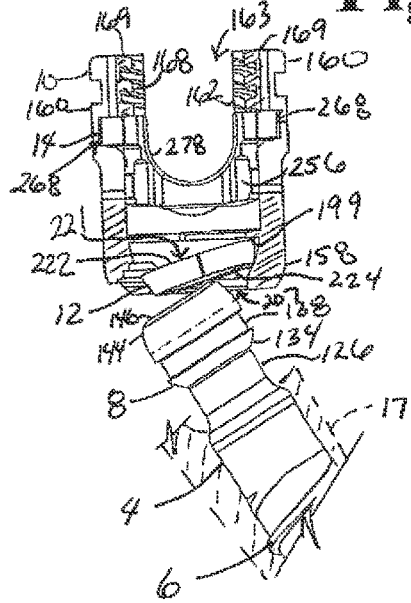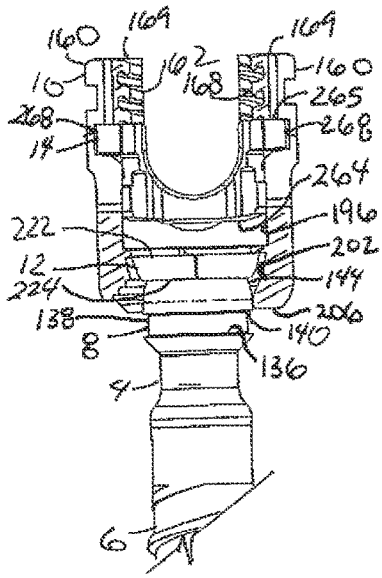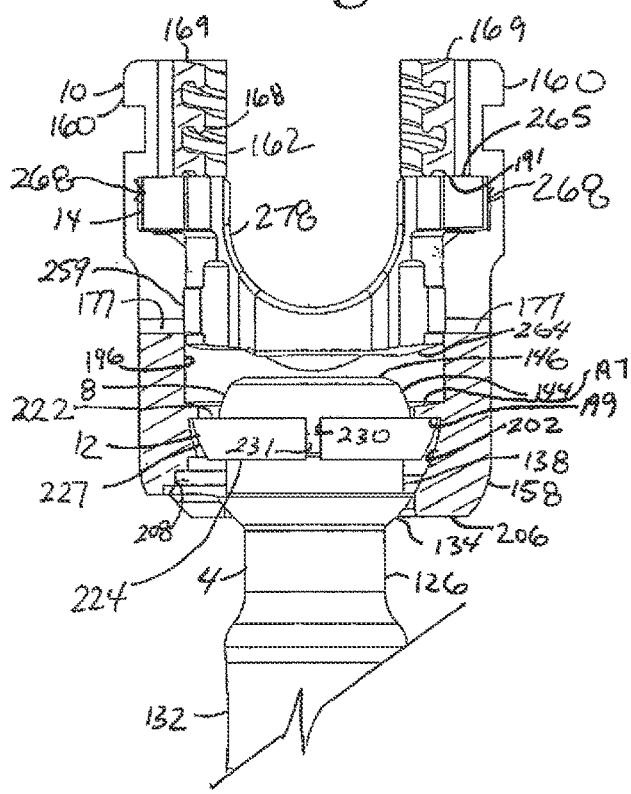

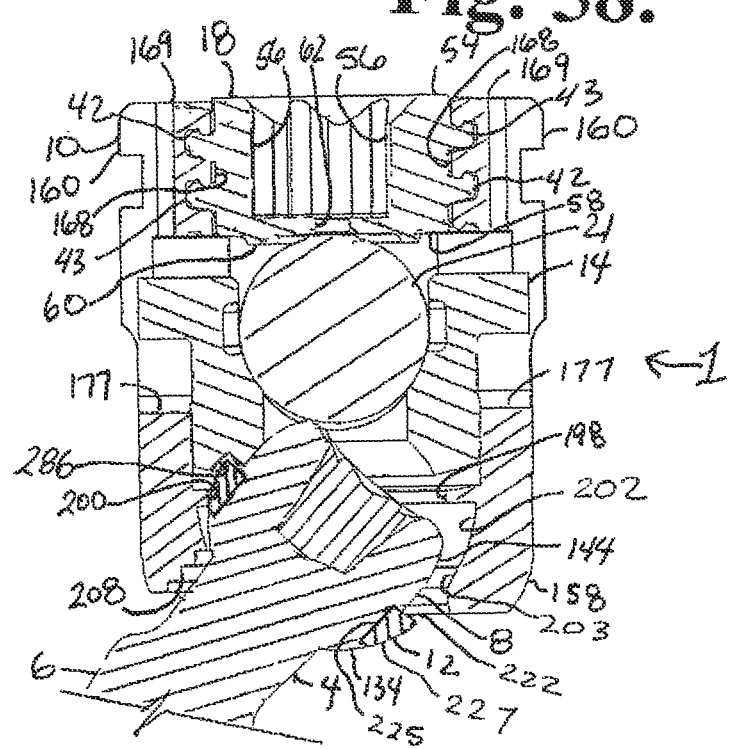

MEDICAL IMPLANT THREAD PLUG HAVING A LOWER ROD ENGAGING EXTENSION

CROSS-REFERENCE TO RELATED APPLICATIONS

The present application is a continuation of U.S. patent application Ser. No. 17/808,438, filed Jun. 23, 2022, which is a continuation of U.S. patent application Ser. No. 17/476,652, filed Sep. 16, 2021, now U.S. Pat. No. 11,399,873, which is a continuation of U.S. patent application Ser. No. 17/123,499, filed Dec. 16, 2020, now U.S. Pat. No. 11,129,646, which is a continuation of U.S. patent application Ser. No. 16/779,304, filed Jan. 31, 2020, now U.S. Pat. No. 10,898,233, which is a continuation of U.S. patent application Ser. No. 15/964,502, filed Apr. 27, 2018, now U.S. Pat. No. 10,548,641, which is a continuation of U.S. patent application Ser. No. 15/469,076, filed Mar. 24, 2017, now U.S. Pat. No. 9,956,004, which is a continuation of U.S. patent application Ser. No. 14/566,356, filed Dec. 10, 2014, now U.S. Pat. No. 9,636,146, which is a continuation of U.S. patent application Ser. No. 13/694,849, filed Jan. 10, 2013, now U.S. Pat. No. 8,911,479, issued Dec. 16, 2014, which claims the benefit of U.S. Provisional Application No. 61/631,746, filed Jan. 10, 2012 and U.S. Provisional Application No. 61/634,361, filed Feb. 28, 2012, all of which are incorporated by reference herein in their entireties for all purposes.

BACKGROUND OF THE INVENTION

The present invention is directed to structure for joining together parts of a medical implant, in particular to closure mechanisms for use with open bone anchors in spinal surgery, and in some embodiments thereof, for use with spinal bone anchors such as polyaxial screws.

Bone anchors, such as bone screws and hooks are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a rod or are supported by the rod. Although both closed-ended and open-ended bone anchors are known, open-ended anchors are particularly well suited for connections to longitudinal connecting members such as hard, soft or deformable rods, dynamic or elastic connectors and connector arms, because such rods or other connector members do not need to be passed through a closed bore, but rather can be laid or urged into an open channel within a receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit.

Typical open-ended bone screws include a threaded shank with a head or receiver having a pair of parallel projecting branches or arms which form a yoke with a U-shaped slot or channel to receive a rod or other longitudinal connecting member. Hooks and other types of connectors, as are used in spinal fixation techniques, may also include similar open ends for receiving rods or portions of other fixation and stabilization structure. The open-ended head or rod receiver portion of such implants typically includes a pair of spaced arms forming a channel closed by a closure member after the rod or other longitudinal connecting member is placed in the channel. Known closures include slide-on types, twist-on varieties that are rotated ninety degrees to a locked in position, and a variety of single start helically wound guide and advancement structures including, for example, thread forms having v-thread, reverse-angle buttress or square thread forms, to name a few, as well as other non-threadlike helically wound forms. Sometimes threaded plugs are utilized with outer threaded nuts to prevent splaying of the receiver arms.

As indicated above, the force required to press a closure structure down onto a rod or other connector located between arms of an open implant is considerable. Even though a head or receiver portion of an open polyaxial bone anchor may be pivoted in a direction to make it easier for the arms of the open implant to receive a rod or other connector, spinal misalignments, irregularities and the placement of other surgical tools make it difficult to place the rod or other connector between the arms of the implant while a closure structure is mated with the open implant as well as used to push the rod or other connector downwardly into the implant. For example, when the closure is a cylindrical plug having a single start helically wound guide and advancement structure, such structure must be aligned with mating structure on one of the implant arms and then rotated until a portion of the structure is captured by mating guide and advancement structure on both arms of the implant, all the while the closure is being pressed down on the rod while other forces are pushing and pulling the rod back out of the implant. Integral or mono-axial open implants that cannot be pivoted to receive the rod are even more difficult to manipulate during the initial placement of the rod and initial mating rotation of a closure plug between the spaced, open arms of the implant. Therefore, extraordinary forces are placed on the implant and closure plug while the surgeon either pushes down on the rod or pulls up on the bone to get the rod in position between the implant arms and to initially push down upon the rod with the closure plug.

SUMMARY OF THE INVENTION

A closure structure, top or plug of the invention for insertion between spaced arms of an open medical implant includes one or more helically wound guide and advancement features, each feature having a start surface or structure located at or near a bottom surface of the closure plug, each start structure simultaneously engaging and being captured by each of the spaced arms of the open implant upon initial rotation of the closure structure with respect to the open implant arms. According to an aspect of the invention, a double-start closure is disclosed having two helically wound forms thereon, each form having a start structure for simultaneously engaging a mating helical form on a respective open implant arm. Each time the illustrated duel- or double-start closure plug is rotated one turn (three hundred sixty degrees) between the implant arms, the closure plug advances axially into the implant and toward the rod by a width of two helical forms. The helically wound forms of the multi-start closure spiral around a cylindrical plug body thereof to an extent that the closure rotates over ninety degrees to fully or substantially receive the entire closure plug between the arms of the open implant. The illustrated closure is sized for at least one complete rotation (three hundred sixty degrees) of the plug with respect to the open implant to substantially receive the plug between the implant arms. Multi-start closures of the invention may have two or more coarse or fine helical forms, resulting in fewer or greater forms per axial distance spiraling about the closure plug body and thus resulting in plugs that rotate less (when more coarse) or more (when thin or fine) than one complete rotation to be fully received between the implant arms, typically, at least a ninety-one degree rotation is preferred.

An illustrated multi-start closure and mating open implant is in the form of non-threaded, interlocking flange forms. Also disclosed are multi-start closure structures provided with helically wound forms of other geometry, including, but not limited to helically wound threads such as reverse angle, buttress, square and v-threads. The multi-start closure may be cannulated for minimally invasive surgical applications.

Another illustrated multi-start closure embodiment of the invention is shown with a bone screw assembly having an open receiver with a pair of opposed arms, each arm having guide and advancement structure for simultaneous mating engagement with a start of the helically wound multi-start closure. A further embodiment according to the invention includes an open bone anchor receiver having integral upwardly extending break-off tabs that also have the guide and advancement structure for mating with the multi-start closure. A further embodiment includes an attachable/detachable guide tool cooperating with such a multi-start open receiver, the tool having inner guide and advancement structures located near a bottom thereof for rotatably and matingly receiving the multi-start closure and being synchronized with the receiver guide and advancement structure for rotating and driving the multi-start closure downward from the guide tool to the receiver.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 18 is an exploded perspective view of the polyaxial bone screw assembly of FIG. 8.

FIG. 19 is an enlarged perspective view of the receiver of FIG. 18.

FIG. 20 is a top plan view of the receiver of FIG. 19.

FIG. 25 is an enlarged cross-sectional view taken along the line 25-25 of FIG. 20.

FIG. 26 is an enlarged perspective view of the retainer of FIG. 18.

FIG. 27 is a top plan view of the retainer of FIG. 16.

FIG. 28 is a bottom plan view of the retainer of FIG. 26.

FIG. 36 is an enlarged cross-sectional view taken along the line 36-36 of FIG. 32.

FIG. 37 is an enlarged front elevational view of the receiver and retainer of FIG. 18 with portions of the receiver broken away to show the detail thereof and shown in an early stage of assembly with the retainer.

FIG. 38 is a front elevational view with portions broken away of the receiver and retainer, similar to FIG. 37, further showing the retainer and also the compression insert of FIG. 18 in a later stage of assembly, the compression insert shown in side elevation.

FIG. 39 is a reduced front elevational view with portions broken away, similar to FIG. 38, showing the insert in a stage of being rotated into a desired position within the receiver.

FIG. 40 is a reduced front elevational view with portions broken away, similar to FIG. 39 showing the insert being rotated into the desired position.

FIG. 41 is an enlarged and partial perspective view of the assembly as shown in FIG. 40, further showing portions of the receiver pressed or crimped toward the insert to prohibit further rotation of the insert with respect to the receiver.

FIG. 42 is an enlarged and partial, partially exploded front elevational view of the shank of FIG. 18 and also the receiver, retainer and compression insert of FIG. 18 as assembled as in FIG. 32, with portions broken away to show the detail thereof, the shank being shown implanted in a vertebra, shown in phantom, as the shank may be assembled with the receiver either before or after implantation.

FIG. 43 is a partial front elevational view, similar to FIG. 42, with portions broken away to show the detail thereof and showing the shank in a stage of assembly with the retainer.

FIG. 44 is an enlarged partial front elevational view, similar to FIG. 43, with portions broken away to show the detail thereof and showing the shank in a subsequent stage of assembly with the retainer wherein the retainer is at maximum expansion with the receiver cavity.

FIG. 45 is a reduced and partial front elevational view, similar to FIG. 44, with portions broken away to show the detail thereof wherein the shank is fully assembled with the retainer.

FIG. 58 is an enlarged front elevational view of the assembly of FIG. 57 with portions broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Furthermore, the terms lead, pitch and start, as such terms are used to describe helically wound guide and advancement structures, are to be understood as follows: Lead is a distance along the axis of a closure plug that is covered by one complete rotation (360 degrees) of the closure plug with respect to a mating open implant. Pitch is the distance from a crest (or outer point or location) of one guide and advancement structure form to the next. For example in a single-start thread-form, such as a single start, helically wound v-thread closure plug, lead and pitch are the same. Single start means that there is only one ridge or helically wound form wrapped around a cylindrical core, or in the case of the present invention, wrapped around a cylindrical closure plug body and thus there is only one start structure or surface at a base or forward end of the closure body that initially engages a mating structure on the open implant. Each time a single start closure rotates one turn (360 degrees), the closure has advanced axially by a width of one ridge or one helical form. Double-start means that there are two ridges or forms wrapped around a core body and thus there are two starting surfaces or structures on the closure plug. Therefore, each time a double-start body rotates one turn (360 degrees), such a body has advanced axially by a width of two ridges or forms. Multi-start means that there are at least two and may be up to three or more of such ridges or forms wrapped around a core body.

Figure 8:
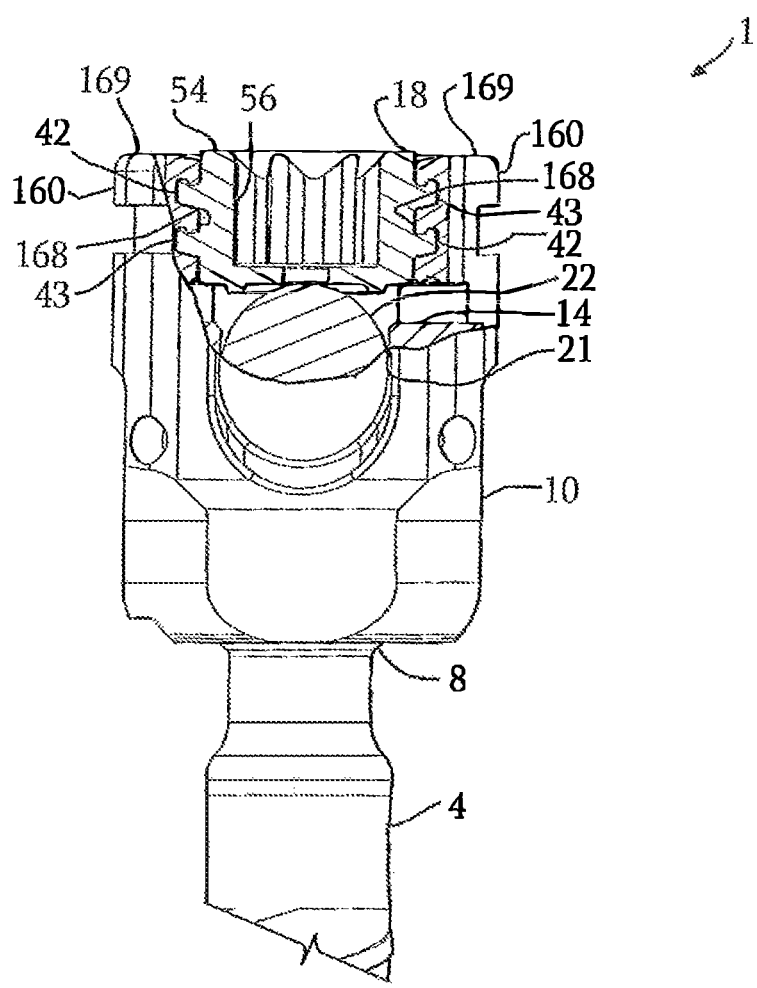
FIG. 8 a partial front elevational view of an open bone screw assembly, with portions broken away to show the detail thereof, including a receiver, a shank, a compression insert and also shown in engagement with the closure top of FIG. 1 (in reduced view) and a longitudinal connecting member in the form of a hard rod.

With reference to FIGS. 1-8 and 18-58, and in particular to FIGS. 8 and 18, the reference number 1 generally represents an open implant in the form of a polyaxial bone screw apparatus or assembly that includes a shank 4, that further includes a body 6 integral with an upwardly extending upper portion or capture structure 8; a receiver 10; a retaining structure or retainer 12, a compression or pressure insert 14, and a multi-start closure structure or plug 18 of the invention in the form of a cylindrical plug having a double start helically wound flange-form. It is noted that multi-start closure embodiments of the invention, such as the closure 18 may be used with a variety of open implants including, but not limited to a wide variety of polyaxial screws, mono-axial or fixed screws, hooks and other types of open implants requiring a plug or closure mechanism to fix a rod or other implant member to a vertebra or other bone. Thus, the assembly 1 is only one example of how multi-start closures of the invention may be used.

The closure structure 18 presses against and captures a longitudinal connecting member, for example, a rod 21 which in turn engages the compression insert 14 that presses against the shank upper portion 8 that is attached to the retaining structure that in turn presses against an inner surface of the receiver 10, so as to capture and fix the longitudinal connecting member 21 within the receiver 10 and thus fix the member 21 relative to a vertebra (not shown). The illustrated receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The illustrated rod 21 is hard, stiff, non-elastic and cylindrical, having an outer cylindrical surface 22. However, in other embodiments, the rod 21 may be elastic, deformable and/or of a different cross-sectional geometry. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes. Furthermore, in lieu of a rod, longitudinal connecting members for use with the assembly 1 may take a variety of shapes, and/or may include a tensioned cord as described in greater detail herein.

It is noted that the receiver 10 includes guide and advancement structures 168 that are shown as interlocking flange forms described in greater detail in applicant's U.S. Pat. No. 6,726,689, also incorporated by reference herein. Alternately, when the closure structure includes a different helical form, the receiver cooperating structures (e.g., 168) must also be of a cooperating, mating geometry, such as a square-shaped thread receiving form, a buttress thread receiving form, a reverse angle thread receiving form or other thread-like or non-thread-like helically wound discontinuous advancement structure receiving forms for operably guiding under rotation and advancing a multi-start closure structure downward between the receiver arms 160, as well as eventual torqueing when the closure structure abuts against the rod 21 or other connecting member.

With particular reference to FIGS. 1-7, the illustrated multi-start closure structure 18 is a double start closure having a substantially cylindrical plug body 40 having an axis of rotation that is the same as that of the receiver 10 and including a helically wound guide and advancement structure in the form of a pair of helically wound forms 42 and 43, each illustrated as an interlocking flange form that operably joins with mating flange form guide and advancement structures 168 disposed on the arms of the receiver 10. The form 42 includes a start surface or structure 46 and the form 43 includes a start surface or structure 47. Each helically wound form 42 and 43 may take a variety of forms and geometries, including those described in Applicant's U.S. Pat. No. 6,726,689, which is incorporated by reference herein. It is noted (and also described in greater detail subsequently herein) that each of the closure structure guide and advancement structures or forms 42 and 43 could alternatively be in the form of a buttress thread, a square thread, a reverse angle thread, a v-thread or other thread like or non-thread like helically wound advancement structures, for operably guiding under rotation and advancing the closure structure downward between the arms of the receive 10 and preferably having such a nature as to resist splaying of the receiver arms when the closure structure 18 is advanced into the receiver channel. The specific flange forms 42 and 43 illustrated in FIGS. 1-7, as well as acceptable alternative locking forms, are described in detail in Applicant's U.S. Pat. No. 6,726,689, incorporated by reference herein, and thus shall not be discussed further herein. Such interlocking flange forms are preferred as the added strength provided thereby beneficially cooperate with and counter any reduction in strength caused by the any reduced profile of the receiver 10 that may more advantageously engage longitudinal connecting member components.

The illustrated closure structure 18 also includes a top surface 54 with an internal drive 56 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 56 is used for both rotatable engagement and, if needed, disengagement of the closure 18 from the receiver 10 at arms 160. It is also foreseen that the closure structure 18 may alternatively include a break-off head designed to allow such a head to break from a base of the closure at a preselected torque, for example, 70 to 140 inch pounds. Such a closure structure would also include a body surface having an internal drive to be used for closure removal. A base or bottom surface 58 of the closure is planar and further includes a rim 60 for engagement and penetration into the surface 22 of the rod 21 in certain embodiments of the invention. The closure top 18 further includes a cannulation through bore 62 extending along a central axis thereof and through a drive base surface 63 and the bottom surface 58 thereof. Such a through bore provides a passage through the closure 18 interior for a length of wire (not shown) inserted therein to provide a guide for insertion of the closure top into the receiver arms 160.

Figure 1:
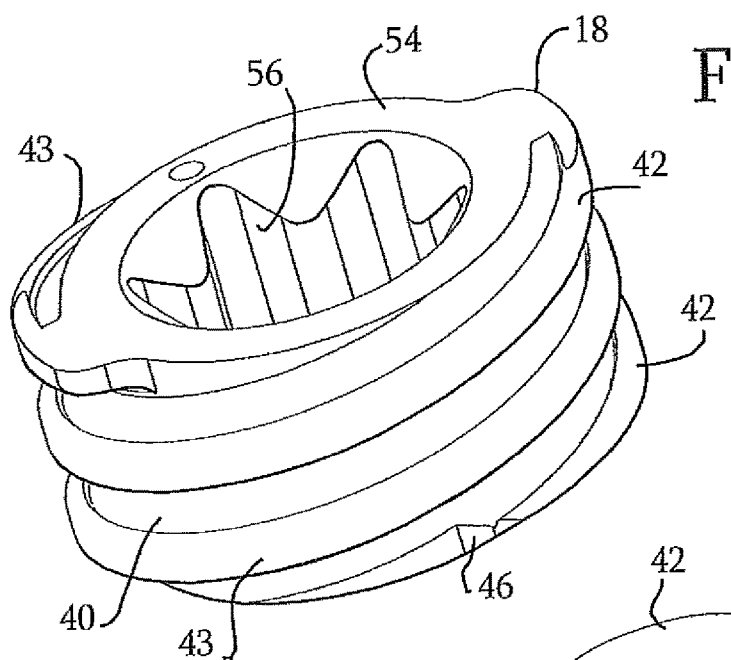
FIG. 1 is a perspective view of an embodiment of a multi-start closure according to the invention.
Figure 2:
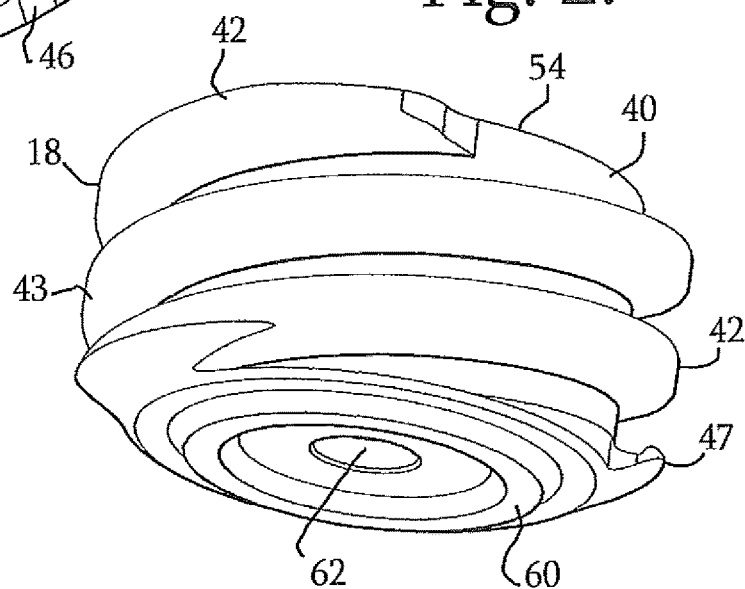
FIG. 2 is another perspective view of the multi-start closure of FIG. 1.
Figure 3:
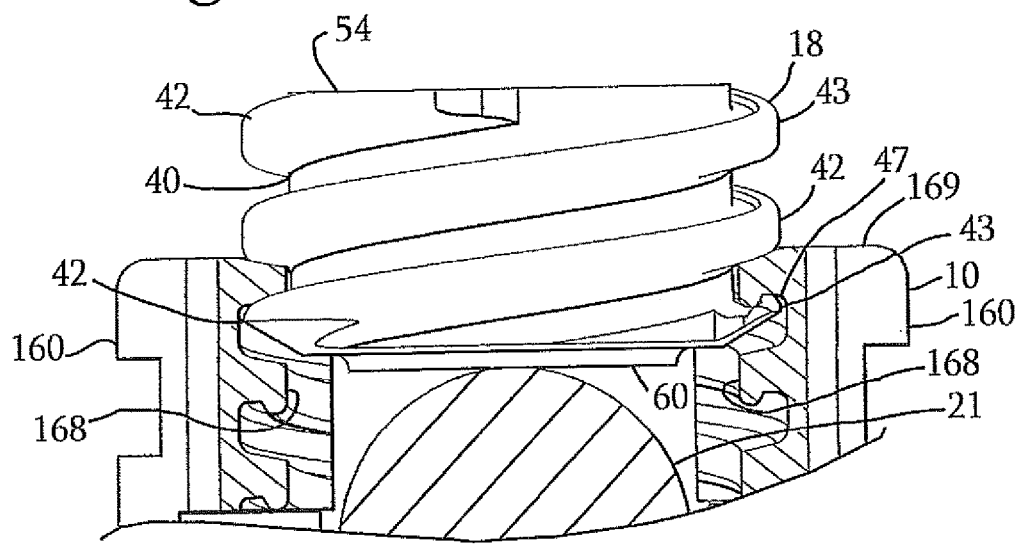
FIG. 3 is a front elevational view of the closure of FIG. 1 shown with a portion of a receiver of a polyaxial bone screw according to FIG. 8, the receiver shown in partial front elevation with portions broken away to show the detail thereof, and further showing a rod being pressed upon by the closure, the rod also in partial front elevation with portions broken away to show the detail thereof.
Figure 4:
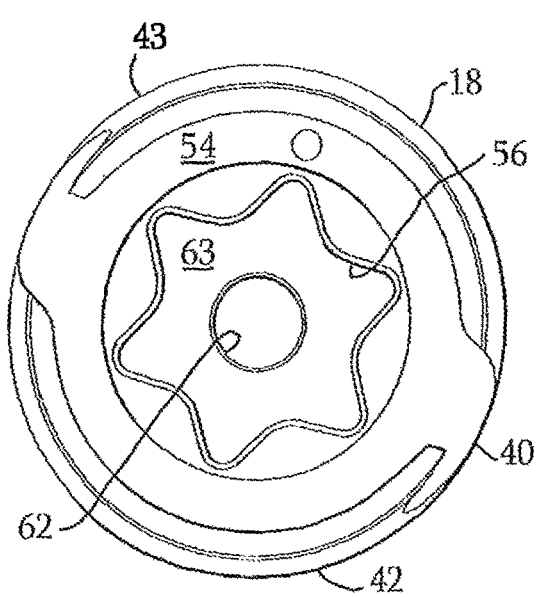
FIG. 4 is a reduced top plan view of the closure of FIG. 1.
Figure 5:
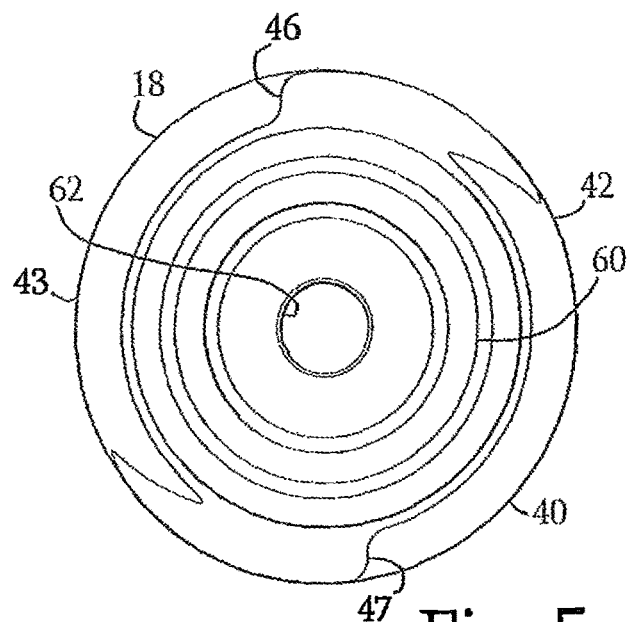
FIG. 5 is a reduced bottom plan view of the closure of FIG. 1.
Figure 6:
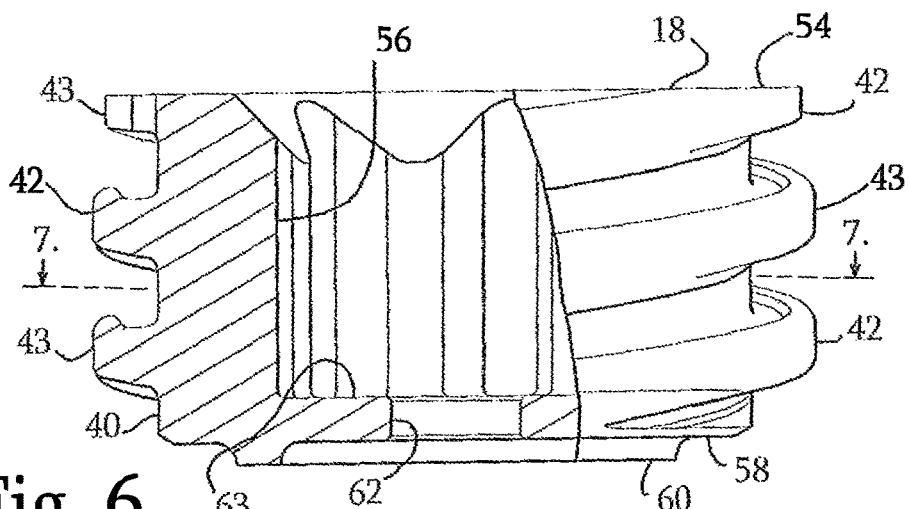
FIG. 6 is an enlarged front elevational view of the closure of FIG. 1 with portions broken away to show the detail thereof.
Figure 7:
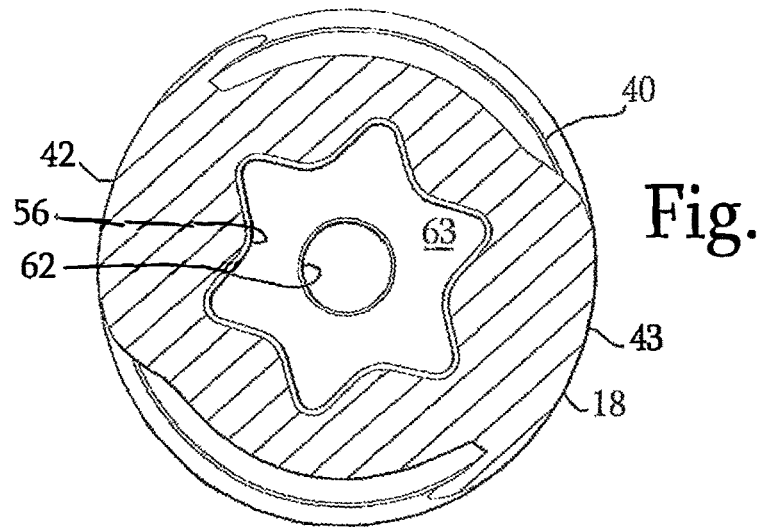
FIG. 7 is a reduced cross-sectional view taken along the line 7-7 of FIG. 6.

The closure structure 18 helically wound flange form start structures 46 and 47 of the respective forms 42 and 43 are located on opposite sides of the closure plug body 40 and are both located adjacent the bottom surface 58. As illustrated in FIG. 3, for example, when the closure structure 18 is rotated into the receiver 10 between receiver arms 160, each having a guide and advancement structure 168, the start 46 engages mating guide and advancement structure 168 on one arm 160 and the start 47 simultaneously engages guide and advancement structure 168 on the opposing arm 160, both forms 42 and 43 being simultaneously captured by the mating forms 168 on the opposed arms 160. As the structure 18 is rotated, the structure advances axially downwardly between the arms 160 and presses evenly down upon the captured rod 21. Each time the illustrated duel- or double-start closure plug 18 is rotated one complete turn or pass (three hundred sixty degrees) between the implant arms, the closure plug 18 advances axially into the implant and toward the rod by a width of two helical flange forms. The illustrated closure 18 is sized for at least one complete rotation (three hundred sixty degree) of the plug 18 with respect to the receiver 10 open arms 160 to substantially receive the plug between the implant arms. Each of the start structures 46 and 47 includes a leading face having at least one curvate surface. The at least one curvate surface includes at least one radius of curvature. In one embodiment, the at least one curvate surface is both concave and convex. Multi-start closures of the invention may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms of the multi-start closure of the invention are sized so as to spiral around a cylindrical plug body thereof to an extent that the closure rotates at least ninety-one degrees to fully or substantially receive the closure plug between the arms of the bone screw receiver or other open implant. Particularly preferred guide and advancement structures are sized for at least one complete turn or pass (three-hundred sixty degree) of the closure between the receiver 10 arms and as many as two to three rotations to be fully received between implant arms.

Figure 50:
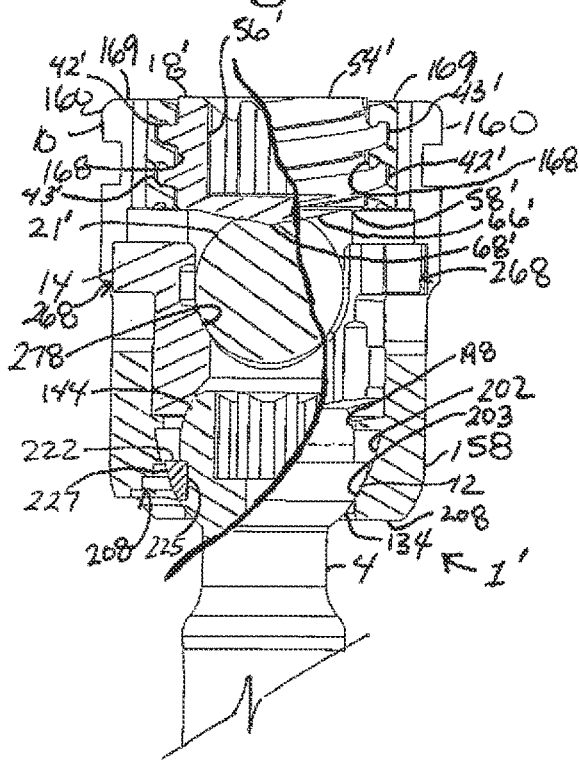
FIG. 50 a reduced and partial front elevational view with portions broken away of the assembly of FIG. 49, but with the rod and closure top thereof removed and replaced with an alternative deformable rod and an alternative multi-start closure of the invention, the insert remaining locked against the receiver and thus keeping the shank locked in place during removal and replacement of the rod and closure top.

An alternative closure top, such as the top 18' shown in FIG. 50 for use with a deformable rod, such as a PEEK rod 21', for example, includes a bottom surface 58' that has a domed portion 66' with a central nub 68' in lieu of the flat and rimmed surfaces of the closure top 18. Otherwise, the closure top 18' includes a guide and advancement structures 42' and 43', a top surface 54' and an internal drive feature 56' the same or substantially similar to the respective guide and advancement structures 42 and 43, top surface 54 and internal drive feature 56 of the closure top 18.

The shank 4, best illustrated in FIGS. 18 and 42-49, is elongate, with the shank body 6 having a helically wound bone implantable thread 124 (single or dual lead thread form) extending from near a neck 126 located adjacent to the upper portion or capture structure 8, to a tip 128 of the body 6 and extending radially outwardly therefrom. During use, the body 6 utilizing the thread 124 for gripping and advancement is implanted into the vertebra 17 leading with the tip 128 and driven down into the vertebra with an installation or driving tool (not shown), so as to be implanted in the vertebra to near the neck 126, as more fully described in the paragraphs below. The shank 4 has an elongate axis of rotation generally identified by the reference letter A.

The neck 126 extends axially upward from the shank body 6. The neck 126 may be of the same or is typically of a slightly reduced radius as compared to an adjacent upper end or top 132 of the body 6 where the thread 124 terminates. Further extending axially and outwardly from the neck 126 is the shank upper portion 8 that provides a connective or capture apparatus disposed at a distance from the upper end 132 and thus at a distance from the vertebra 17 when the body 6 is implanted in such vertebra.

The shank upper portion 8 is configured for a pivotable connection between the shank 4 (with attached retainer 12) and the receiver 10 prior to fixing of the shank 4 in a desired position with respect to the receiver 10. The shank upper portion 8 has an outer, convex and substantially spherical lower surface 134 that extends outwardly and upwardly from the neck 126 and terminates at a substantially planar ledge or shelf 136 that is annular and disposed perpendicular to the shank axis A. The spherical lower surface 134 has an outer radius that is the same or substantially similar to an outer radius of the retainer 12 as will be described in greater detail below, the surface 134 as well as the retainer 12 outer surface participating in the ball and socket joint formed by the shank 4 and attached retainer 12 within the partially spherical surface defining an inner cavity of the receiver 10. Extending upwardly from the ledge 136 is a cylindrical surface 138, the surface 138 having a radius that is smaller than the radius of the lower spherical surface 134. Extending outwardly from the cylindrical surface 138 is another annular surface or upper ledge 140 that faces toward the ledge 136 and is also substantially perpendicular to the axis A. As will be discussed in greater detail below, the lower ledge 136, cylindrical surface 138 and upper ledge 140 cooperate to capture and fix the resilient open retainer 12 to the shank upper portion 8, prohibiting movement of the retainer 12 along the axis A once the retainer 12 is located between the ledges 136 and 140. Extending upwardly from the upper ledge 140 is a cylindrical surface 142 having a radius smaller than the radius of the spherical surface 134 but larger than the radius of the cylindrical surface 138. Extending upwardly from the surface 142 is an upper partially spherical or domed surface 144. The spherical surface 144 has an outer radius configured for sliding cooperation and ultimate frictional mating with a substantially spherical concave surface of the compression insert 14 that has the same or substantially similar radius as the surface 144. The radius of the surface 144 is smaller than the radius of the lower spherical surface 134. Located near or adjacent to the surface 144 is an annular top surface 146. In the illustrated embodiment a bevel 147 extends about the spherical surface 144 and is located between the spherical surface 144 and the annular planar top surface 146.

A counter sunk substantially planar base or seating surface 149 partially defines an internal drive feature or imprint 150. The illustrated internal drive feature 150 is an aperture formed in the top surface 146 and has a multi-lobular or star-shaped aperture, such as those sold under the trademark TORX, the aperture designed to receive a tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or hex shape, or other geometric shape. The seat or base 149 of the drive feature 150 is disposed perpendicular to the axis A with the drive feature 150 otherwise being coaxial with the axis A. In operation, a driving tool is received in the internal drive feature 150, being seated at the base 149 and engaging the faces of the drive feature 150 for both driving and rotating the shank body 6 into the vertebra 17, either before the shank 4 is attached to the receiver 10 as shown in FIG. 42 or after the shank 4 is attached to the receiver 10, with the shank body 6 being driven into the vertebra 17 with the driving tool extending into the receiver 10.

The shank 4 shown in the drawings is cannulated, having a small central bore 151 extending an entire length of the shank 4 along the axis A. The bore 151 is defined by an inner cylindrical wall of the shank 4 and has a circular opening at the shank tip 128 and an upper opening communicating with the internal drive 150 at the surface 149. The bore 151 is coaxial with the threaded body 6 and the upper portion 8. The bore 151 provides a passage through the shank 4 interior for a length of wire (not shown) inserted into the vertebra 17 prior to the insertion of the shank body 6, the wire providing a guide for insertion of the shank body 6 into the vertebra 17.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 18-25, the receiver 10 has a generally U-shaped appearance with a partially discontinuous substantially cylindrical inner profile and a partially cylindrical and partially faceted outer profile. The receiver 10 has an axis of rotation B that is shown in FIG. 18 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIGS. 54-58.

The receiver 10 includes a substantially cylindrical base 158 integral with a pair of opposed upstanding arms 160. A cavity, generally 161, is located within the base 158. The arms 160 form a cradle and define a U-shaped channel 162 with an upper opening, generally 163, and a U-shaped lower seat 164, the channel 162 having a width for operably snugly receiving the rod 21 between the arms 160. The channel 164 communicates with the base cavity 161. Each of the arms 160 has an interior surface, generally 166 that has a cylindrical profile and further includes a partial helically wound guide and advancement structure 168 extending radially inwardly from the surface 166 and located adjacent top surfaces 169 of each of the arms 160. In the illustrated embodiment, the guide and advancement structures 168 are each in the form of a partial helically wound interlocking flange form configured to mate under rotation with the dual start closure structure 18. Thus, unlike single start advancement structures, the helical forms 168 on the opposing arm surfaces 166 that are configured to mate with the dual start closure top 18 are reverse or flipped images of one another, the structures 168 on each arm 160 being aligned with respect to the receiver axis B, so that each closure structure start and are simultaneously engaged and captured at each arm 160 at the same time.

The arms 160 further include an opposed pair of vertically extending outer grooves, generally 174, running substantially parallel to the receiver axis B that are centrally formed in outer curved (illustrated as faceted, both curved and planar) surfaces 176. Each groove 174 runs centrally from the respective arm top surface 169 and terminates at a through aperture 177. Each aperture 177 extends through the respective arm surface 176 and also through the respective interior arm surface 166 and is located spaced from the receiver base 158. Each groove 174 has an upper opening partially defined by a pair of opposed surfaces 179 and a substantially planar outer wall surface 181 extending between the surfaces 179. The planar wall surface 181 terminates at the top arm surface 169 and at a lower surface 182 partially defining the aperture 177. The illustrated opposed surfaces 179 are parallel and extend below the lower surface 182, partially defining the through aperture 177. The opposed surfaces 179 are sized to receive portions of an elongate tool (not shown) for locking and unlocking the insert 14 with respect to the receiver as will be described in greater detail below. In some embodiments, the surfaces 179 may be disposed at a slight angle with respect to each other, forming a dovetail-like space for maintaining a close relationship between an elongate tool (not shown) that enters into the groove 174 at the arm top surface 169 and is slidingly received between the surfaces 179. The surfaces 179 terminate at a lower surface 183 that also partially defines the through aperture 177. The surface 183 is substantially perpendicular to the surfaces 179. Thus, the illustrated through aperture 177 located below each of the grooves 174 is substantially the same width as the groove 174 there-above, resulting in the aperture 177 having a substantially rectangular profile. The through apertures 177 are sized and shaped for receiving tooling and portions of the compression insert 14 as will be described in greater detail below.

With particular reference to FIGS. 19, 22, 24, and 41, formed in the arm surfaces 176 and located on either side of the through apertures 177 are lateral crimping apertures 186. The four crimping apertures 186 are substantially circular in profile and do not extend completely through the respective arms 160, but rather terminate at a location between the arm outer surface 176 and the interior surface 166 to provide a crimping portion or wall 187. The crimping portions or walls 187 are sized and shaped for pressing or crimping some or all of the wall material inwardly onto front and rear surfaces of the insert 14 to prohibit rotation and misalignment of the insert 14 with respect to the receiver 10 as will be described in greater detail below.

The receiver 10 is a one-piece or integral structure and is devoid of any spring tabs or collet-like structures. Preferably the insert and/or receiver are configured with structure for blocking rotation of the insert with respect to the receiver, such as the crimp walls 187, but allowing some up and down movement of the insert with respect to the receiver during the assembly and implant procedure. Also formed in each outer arm surface 176 near the top surface 169 is an undercut tool receiving and engaging groove 189. Some or all of the apertures and grooves described herein, including, but not limited to grooves 174, apertures 177, and grooves 189 may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of inserts according to the invention with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arm 160 outer surfaces 176 and/or inner surfaces 166 as well as surfaces defining the base 158.

Returning to the interior arm surfaces, generally 166, of the receiver arms 160, located below the discontinuous guide and advancement structure 168 is a discontinuous cylindrical surface 190 partially defining a run-out feature for the guide and advancement structure 168. Adjacent to and above the surface 190 is a discontinuous upper annular ceiling surface 191. The upper annular surface 191 includes the surface 182 that partially defines the aperture 177 and also includes bottom surfaces of the guide and advancement structure 168. Also adjacent to and below the surface 190 is a discontinuous annular surface or step 192 that in turn is adjacent to a discontinuous frusto-conical surface 193 that extends from the surface 192 inwardly toward the receiver central axis B. Adjacent the surface 193 is another substantially cylindrical discontinuous surface 194 that may in some embodiments run frusto-conical either toward or away from the axis B, depending upon, for example, clearance requirements for the top loading of assembly components, such as the retainer and a compression insert or inserts and also modifying (enlarging or reducing) a thickness for the crimping walls 187, if desired. In the current embodiment, the surface 194 terminates at a small discontinuous ledge or lip 195 directed inwardly toward the axis B. The through apertures 177 extend through both the cylindrical surfaces 190 and the surfaces 193 and 194. A cylindrical surface 196 is adjacent to and runs downwardly from the lip 195 towards the base cavity 161. A lower portion of the cylindrical surface 196 is continuous and thus partially defines the base cavity 61. The cylindrical surface 196 has a diameter smaller than a diameter of the cylindrical surface 190, but larger than a diameter of the surface 194. The receiver inner arm surfaces 166 may further include other sloped, stepped or chamfered surfaces between the cylindrical surfaces 190, 194, and 196 as desired for ease in assembly of the other top loaded components.

Figure 23:
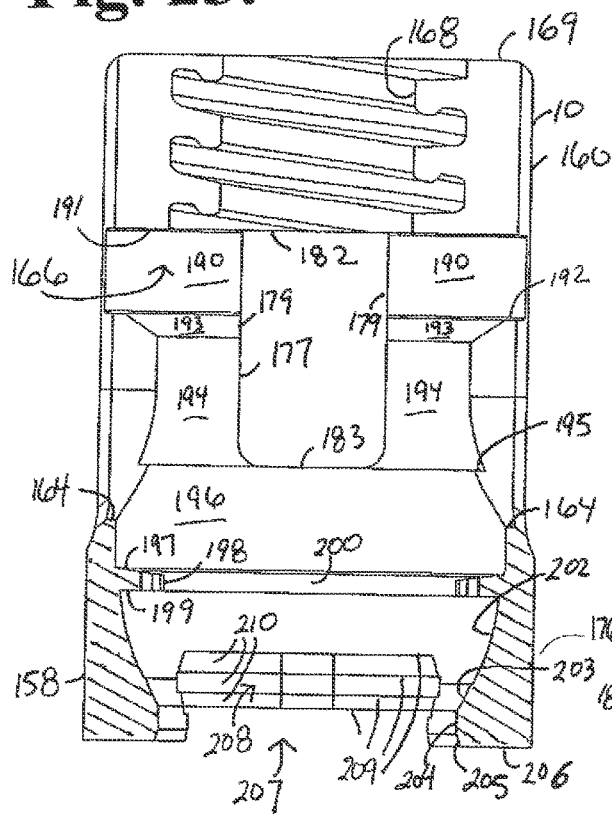
FIG. 23 is an enlarged cross-sectional view taken along the line 23-23 of FIG. 20.
Figure 24:
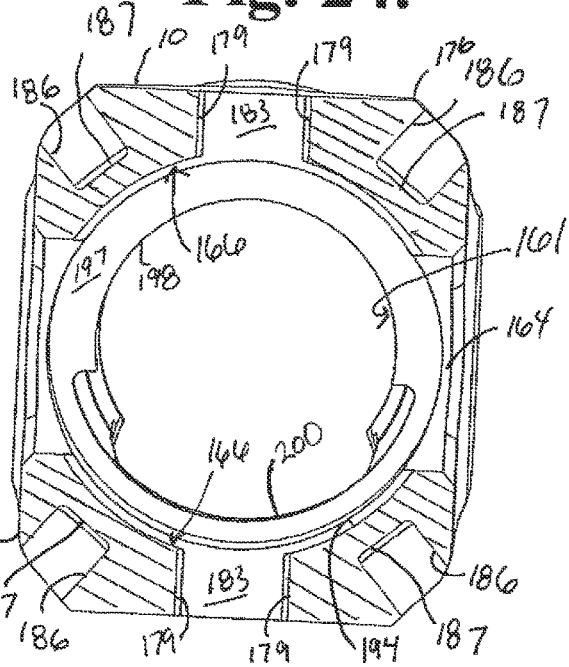
FIG. 24 is an enlarged cross-sectional view taken along the line 24-24 of FIG. 22.
Figure 29:
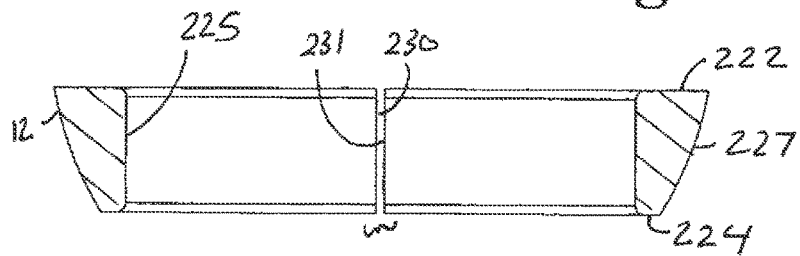
FIG. 29 is an enlarged cross-sectional view taken along the line 29-29 of FIG. 27.
Figure 30:
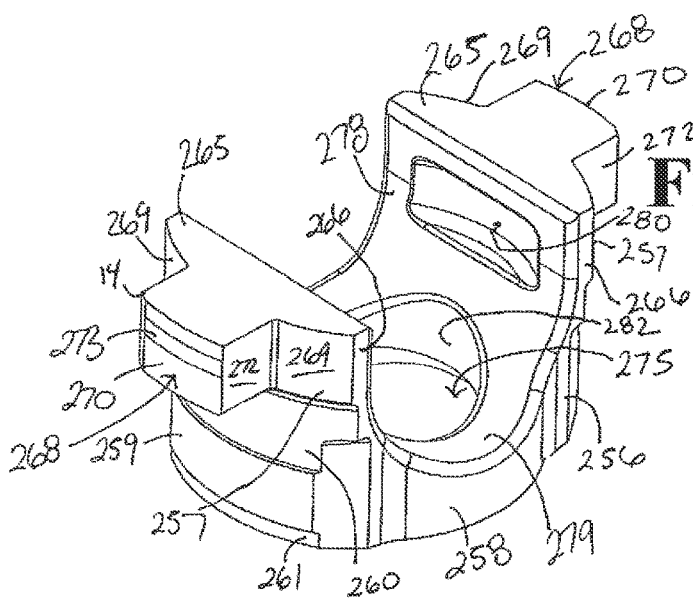
FIG. 30 is an enlarged perspective view of the compression insert of FIG. 18.
Figure 31:
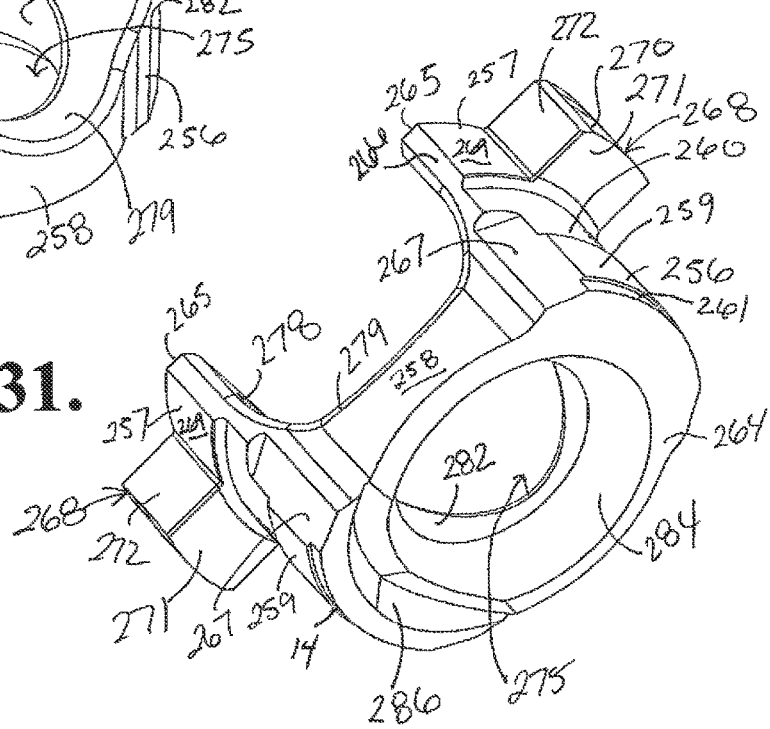
FIG. 31 is another perspective view of the insert of FIG. 30.
Figure 32:
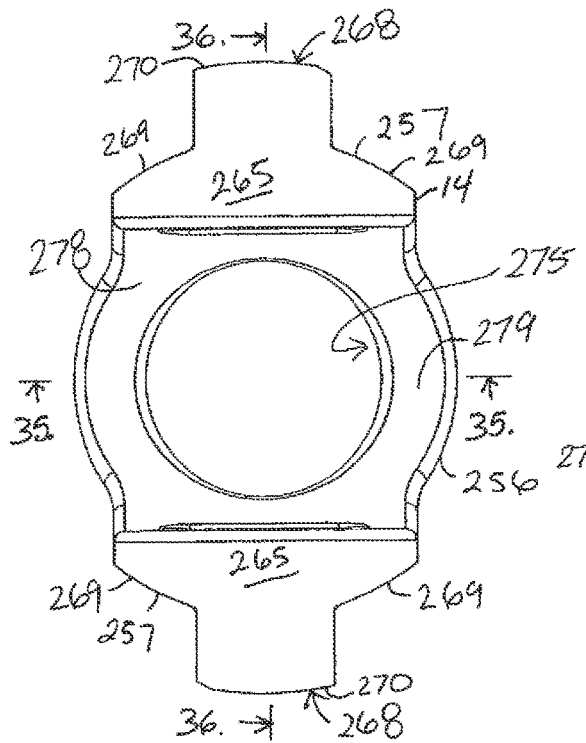
FIG. 32 is a top plan view of the insert of FIG. 30.
Figure 33:
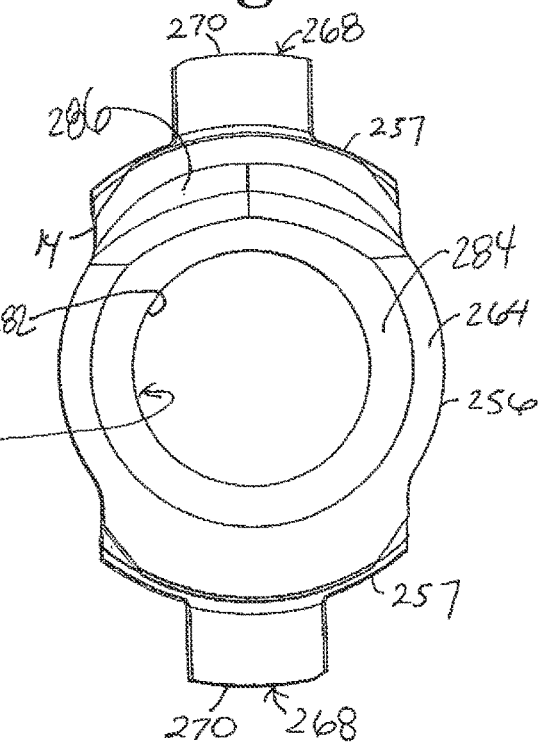
FIG. 33 is a bottom plan view of the insert of FIG. 30.
Figure 34:
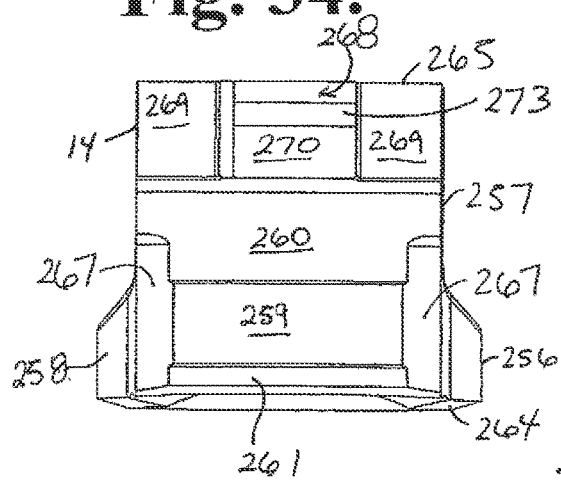
FIG. 34 is a reduced side elevational view of the insert of FIG. 30.
Figure 35:
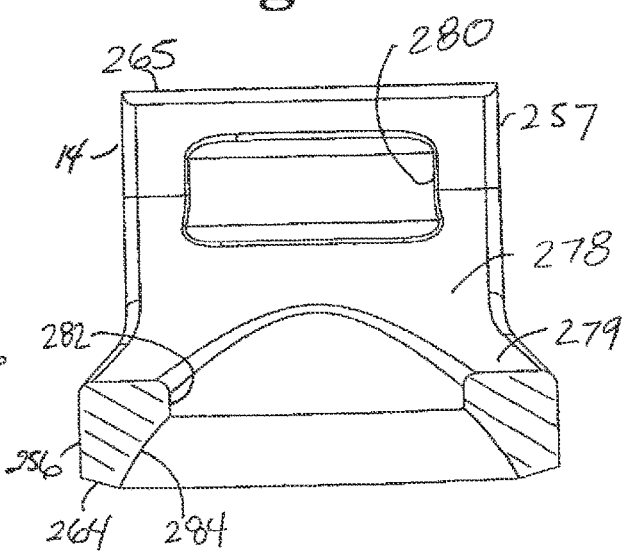
FIG. 35 is an enlarged cross-sectional view taken along the line 35-35 of FIG. 32.

With particular reference to FIGS. 23-25, the continuous portion of the inner cylindrical surface 96 terminates at a downwardly sloping, annular ledge surface 197 that extends from the surface 196 and runs inwardly toward the receiver axis B. The surface 197 terminates at a substantially cylindrical surface 198. The surface 198 terminates at another annular surface 199 that faces a lower portion of the receiver cavity 161. The surfaces 197, 198, and 199 form an abutment or ceiling stop for the retainer 12 as will be described in greater detail below. The ceiling surface 199 runs substantially perpendicular to the axis B. Cut or otherwise formed into the surfaces 197, 198, and 199 under one of the arms 160 is a curved c-shaped notch, creating a substantially cylindrical surface 200 having a radius greater than a radius of the surface 198, the opening partially defined by the surface 200 providing clearance within the assembly 1, allowing the retainer 12 to move above the surface 197 when the shank 4 and attached retainer 12 are pivoted at a favored angle, for example, as shown in FIG. 58 and discussed in more detail below.

As stated above, the surface 199 is substantially annular and defines an upper ceiling or stop of a retainer 12 expansion portion or chamber of the inner cavity 161 that is further defined by a substantially spherical surface 202 that is adjacent to the surface 199. The surface 202 partially defines a recess that is sized and shaped to receive the retainer 12 as it expands around the shank upper portion 8 as the shank 8 is moved upwardly toward the channel 162 during assembly. Located below and adjacent to the spherical surface 202 is another curved surface 203 extending downwardly and inwardly toward the axis B. The surface 203 is illustrated as spherical, but in some embodiments the surface may be frusto-conical. The surface 203 is a seating surface for the retainer 12, the surface 203 slidingly receiving the retainer 12 until the retainer is frictionally locked against the surface 203 when downward pressure is placed on the shank 4 by the insert 14. A cylindrical surface 204 is adjacent the spherical surface 203 and an outwardly flaring surface 205, illustrated as frusto-conical, spans between the cylindrical surface 204 and a bottom surface 206 of the receiver 10. The surface 205 communicating with the bottom surface 206 to define a lower opening, generally 207 into the receiver base inner cavity 161. The cylindrical surface 204, as well as the frusto-conical surface 203 are sized and shaped to be smaller than an upper outer radial dimension of the retainer 12 when the retainer 12 is fixed to the shank upper portion 8, so as to form a restriction to prevent the structure 12 and attached shank portion 8 from passing through the cavity 161 and out the lower exterior 206 of the receiver 10 during operation thereof.

In various embodiments of the invention, a cut-out or aperture made of one or more notches or curved, cupped or stepped surfaces may be cut into or otherwise formed in a portion of the base surface 206, as well as in portions of the surfaces 202, 203, 204, and 205, the cupped or stepped surfaces being typically located substantially centrally and directly below one of the arm 160. Such a cupped or stepped surface or surfaces may be sized and shaped for providing clearance for an increased angle of articulation between the shank 4 and the receiver 10 in a particular or desired direction. In the present embodiment, one such arrangement of stepped surfaces, generally 208 is illustrated. In particular, the cut-out portion 208 includes a plurality of graduated, partially annular surfaces 209 connecting with a plurality of graduated partially planar and partially curved surfaces 210, the surfaces 209 and 210 defining edges for gripping the shank 4 as shown, for example in FIG. 58. The cut-out 208 is located directly below the cut-out portion 200 that provides clearance for the retainer 12 during such a favored angle pivoting of the shank 4 and attached retainer 12.

With particular reference to FIGS. 18 and 26-29, the open retainer 12 that operates to capture the shank upper portion 8 within the receiver 10 has a central axis C that is operationally the same as the axis A associated with the shank 4 when the shank upper portion 8 and the retainer 12 are installed within the receiver 10. The retainer 12 is made from a resilient material, such as a stainless steel or titanium alloy, so that the retainer 12 may be expanded during assembly as will be described in greater detail below. However, because there is little or no need to compress the retainer 12 during assembly, the opening or slit that allows for expansion of the retainer 12 is designed to be very narrow, advantageously providing substantial or almost full surface contact between the retainer and the shank upper portion 8 and also between the retainer and the receiver seating surface 203.

The retainer 12 has a central channel or hollow through bore, generally 221, that passes entirely through the structure 12 from a top surface 222 to a bottom surface 224 thereof. The bore 221 is primarily defined by a discontinuous inner cylindrical surface 225 that runs from the top surface 222 to the bottom surface 224. In some embodiments of the invention, notches or grooves may be formed in the inner and/or bottom surfaces to more evenly distribute stress across the entire retainer during expansion thereof. The retainer 12 further includes an outer substantially spherical surface 227 running between the top surface 222 and the bottom surface 224, the surface 227 has an identical or substantially similar radius as the receiver seating surface 203 and also the shank lower spherical surface 134. The resilient retainer 12 further includes first and second end surfaces, 230 and 231 disposed in spaced relation to one another when the retainer is in a neutral state. Both end surfaces 230 and 231 are disposed substantially perpendicular to the top surface 222 and the bottom surface 224. The embodiment shown in FIGS. 26-29 illustrates the surfaces 230 and 231 as substantially parallel, however, it is foreseen that it may be desirable to orient the surfaces obliquely or at a slight angle to the top and bottom surfaces.

With particular reference to FIGS. 18 and 30-36, the locking compression insert 14 is illustrated that is sized and shaped to be received by and down-loaded into the receiver 10 at the upper opening 166. The compression insert 14 has an operational central axis that is the same as the central axis B of the receiver 10. In operation, the insert advantageously frictionally engages the bone screw shank upper portion 8 as well as engaging the receiver 10 in an interference fit engagement, locking the shank 4 in a desired angular position with respect to the receiver 10 that remains in such locked position even if, for example, a rod and closure top are later removed and the rod is replaced with another rod or other longitudinal connecting member or member component, such as a sleeve of a tensioned cord connecting member. Such locked position may also be released by the surgeon if desired with insert engaging tools (not shown). In some embodiments of the invention, an alternative insert is provided that does not have the receiver interference fit feature, but is otherwise substantially similar to the insert 14. Such an insert includes outer surfaces that are slidingly received along the receiver 10 surfaces defining the arms 160 and the cavity 161. The locking insert 14 (as well as the non-locking alternative insert not shown) is preferably made from a solid resilient material, such as a stainless steel or titanium alloy, so that portions of the insert 14 may be grasped, pinched or pressed, if necessary, and un-wedged from the receiver 10 with a release tool (not shown).

The locking compression insert 14 includes a body 256. with cylindrical surfaces of a variety of diameters as well as planar surfaces and chamfers and cut-outs to provide clearance between the insert 14 and the retainer 12 during various steps of assembly as well as when the assembly 1 is in a final locked position. The body 256 is integral with a pair of upstanding arms 257. Located between the arms 257, the body 256 has an outer partial cylindrical surface 258. Each arm outer surface is substantially cylindrical in profile but is made from a variety of facets or faces as well as cut-outs to provide for clearance with other components of the assembly 1. Located on the body 256 below each upstanding arm 257 is a substantially cylindrical interference fit surface or band 159 that extends outwardly from and between an upper cylindrical surface 260 and a lower cylindrical surface 261. The lower surface 261 is adjacent to an annular bottom surface 264 of the insert 14. Each upper cylindrical surface 260 partially defines one of the insert arms 257. The interference fit band 159 runs substantially parallel to the bottom surface 264. A diameter of the insert 14 measured at the band surface 259 is larger than a diameter measured at surfaces 260 or 261. As best shown in FIG. 36, in the illustrated embodiment, the bottom surface 264 is disposed at an angle with respect to the lower surface 261, but may be perpendicular to the lower surface 261 in other embodiments. The insert 14 further includes substantially planar arm top surfaces 265 located opposite the bottom surface 264. The arms 257 are each further defined by substantially planar front and rear surfaces 266 that run from the top surfaces 265 to the bottom surface 264. At the bottom surface 264, the front and rear surfaces 266 are narrow due to clearance cut-outs 267 located at each corner of the insert 14. Each arm 257 also includes an outwardly extending wing, generally 268 located centrally on and extending outwardly from an upper cylindrical surface 269 of the arm 257, the surface 269 being adjacent to the arm top surface 265. Each arm top surface 265 also extends along the respective wing 268 to a substantially cylindrical outer surface 270. Each wing is also defined by a lower surface 271 and opposed planar side surfaces 272, the upper surfaces 265 and the lower surfaces 271 being substantially parallel to one another. The juncture between the planar side surfaces 272 and the cylindrical surface 270 may include one or more chamfered, planed, or otherwise angled or curved surface to aid in rotational assembly of the insert 14 within the receiver 10. The opposed side surfaces 272 generally span between top and bottom surfaces 265 and 271 respectively, of each wing 268, the side surfaces 272 being substantially perpendicular to adjacent top and bottom surfaces 265 and 271. The cylindrical surfaces 270 are sized and shaped for sliding rotation within the receiver arm cylindrical surfaces 190 during assembly of the insert 14 with the receiver 10 as will be described in greater detail below. The illustrated wings 268 include indicator stripes 273 that provide a surgical staff with an indication of the location of the insert 14 with respect to the receiver 10 during surgery. For example, the location of the stripe 273 with respect to the receiver 10 indicates whether the insert 14 is in a non-floppy, but movable, frictional engagement with the shank head 8 or whether the insert 14 is fully locked down on the shank head 8. The indicator stripes 273 are conveniently located on the wing cylindrical surface 270 that is visible when the wings 268 are extending through the receiver apertures 177.

Returning to the inner surfaces of the insert 14, a through bore, generally 275, is disposed primarily within and through the body 256 and communicates with a generally U-shaped through channel formed by a saddle surface 278 that is substantially defined by the upstanding arms 257. Near the top surfaces 265, the saddle surface 278 is substantially planar. The saddle 278 has a curved lower seat 279 sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved tensioned cord longitudinal connecting member. A pair of opposed, inwardly facing grooves or apertures 280 are located in the saddle 278 beginning near a juncture of the substantially planar upper portion of the saddle 278 and extending toward the curved lower seat 279. The grooves 280 are sized and shaped to receive tooling for rotation, locking, unlocking and other manipulation of the insert 14.

The bore, generally 275, is substantially defined at the body 256 by an inner cylindrical surface 282 that communicates with the seat 279 and also communicates with a lower concave, radiused or otherwise curved portion 284, that in some embodiments may include shank gripping surfaces or ridges, the surface portion 284 generally having a radius for closely mating with the surface 144 of the shank upper portion 8. The portion 284 terminates at the base surface 264. It is foreseen that the lower shank engaging portion 284 may additionally or alternatively include a roughened or textured surface or surface finish, or may be scored, knurled, or the like, for enhancing frictional engagement with the shank upper portion 8. Formed in a portion of the surface 284 and in a portion of the bottom surface 264 is a notch 286 sized and shaped to receive a portion of the retainer 12 when the shank 4 and attached retainer 12 are pivoted into a favored angle position as shown, for example, in FIG. 58. The notch 286 is located directly beneath one of the arms 257 and has a geometry for receiving a portion of the top 222 and outer spherical surface 227 of the retainer 12 when the shank upper portion 8 is fully locked into place by the insert surface 284 and the shank 4 is pivoted toward the receiver cut-out 208.

The compression insert 14 through bore 275 is sized and shaped to receive a driving tool (not shown) therethrough that engages the shank drive feature 146 when the shank body 6 is driven into bone with the receiver 10 attached. Also, in some locking embodiments of the invention, the bore receives a manipulation tool (not shown) used for releasing the insert 14 from a locked position with the receiver 10, the tool pressing down on the shank head 8 and also gripping the insert 14 at the apertures 280, or with other tool engaging features. Each of the arms 257 and the insert body 256 may include more surface features, such as cut-outs notches, bevels, etc. to provide adequate clearance for inserting the insert 14 into the receiver and cooperating with the retainer 12 during the different assembly steps as will be described in greater detail below.

The insert body 256 cylindrical surface 258 has a diameter slightly smaller than a diameter between crests of the guide and advancement structure 168 of the receiver 10, allowing for top loading of the compression insert 14 into the receiver opening 163, with the arms 257 of the insert 14 being located between the receiver arms 160 during insertion of the insert 14 into the receiver 10 as shown, for example, in FIG. 38. Once the arms 257 of the insert 14 are generally located beneath the guide and advancement structure 168, the insert 14 is rotated into place about the receiver axis B with the wings 268 entering the receiver groove formed by the cylindrical surface 190, the adjacent upper annular surface 191 and the adjacent lower annular surface 192 until the wings 268 are located in the apertures 177 as will be described in greater detail below.

With reference to FIGS. 18 and 48-50, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

Preferably, the receiver 10, the retainer 12 and the compression insert 14 are assembled at a factory setting that includes tooling for holding, alignment and manipulation of the component pieces, as well as crimping a portion of the receiver 10 toward the insert 14. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point (see, e.g., FIG. 42). In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost.

Pre-assembly of the receiver 10, retainer 12 and compression insert 14 is shown in FIGS. 37-41. With particular reference to FIG. 37, first the retainer 12 is inserted into the lower receiver opening 207, leading with the outer surface 227, the top surface 222 slightly angled to face upwardly and toward one arm 160 that is located above the stepped, cut-out 208. The retainer 12 is then moved upwardly and at an angle toward the annular ceiling surface 199 located opposite the cut-out surface 200 and then past the stepped cut-out 298 in such an angled and upward manner into the chamber 161, followed by tilting the retainer 12 such that the top surface 222 is moved into a position within the receiver cavity 161 axially aligned with the receiver axis B and spaced from the surface 199. Then the retainer 12 is allowed to drop until the retainer spherical surface 227 is seated on the receiver spherical surface 203 as shown in FIG. 38.

Also with reference to FIG. 38 and with further reference to FIGS. 39 and 40, the. compression insert 14 is then downloaded into the receiver 10 through the upper opening 163 with the bottom surface 264 initially facing the receiver arm top surfaces 169 and the insert arms 257 located between the opposed receiver arms 160. The insert 14 is then lowered toward the channel seat 164 until the insert 14 arm upper surfaces 265 are adjacent the receiver arm inner surfaces located below the guide and advancement structures 168. Thereafter, the insert 14 is rotated in a clockwise or counter-clockwise manner about the receiver axis B until the upper arm surfaces 265 are directly below the guide and advancement structure 168 of each arm as illustrated in FIG. 40 with the U-shaped channel 278 of the insert 14 aligned with the U-shaped channel 162 of the receiver 10. In some embodiments, the insert arms 257 may need to be compressed slightly during rotation to clear inner surfaces of the receiver arms 160. As the insert 14 is rotated about the axis B, the insert wings, generally 268 slidingly rotate within the circular groove formed by the receiver surfaces 190, 191, and 192.

With particular reference to FIGS. 40 and 41, at this time, the four crimping wall portions 187 are pressed inwardly towards the insert 14 and crimping wall material thus engages the insert near front and rear surfaces 266 thereof, specifically at the four surfaces or facets 267 as best shown in FIG. 41. The crimping wall material of the wall 187 pressing against the insert 14 at a total of four locations thereby prohibits the insert 14 from rotating with respect to the receiver axis B. At this time, there can be some upward and downward movement of the insert 14, but such movement is limited as the upper wall 182 defining the receiver aperture 177 (that is also the surface 191) stops further upward movement of the insert wings 268. Downward movement of the insert 14 is prohibited by the bands 259 resting on receiver ledge surface 195 adjacent the cylindrical surface 196. The retainer 12 and the insert 14 are now in a desired position for shipping as an assembly along with the separate shank 4 and also ready for assembly with the shank 4 either at the factory, by surgery staff prior to implantation, or directly upon an implanted shank 4 as will be described herein.

As illustrated in FIG. 42, the bone screw shank 4 or an entire assembly 1 made up of the assembled shank 4, receiver 10, retainer 12 and compression insert 14, is screwed into a bone, such as the vertebra 17, by rotation of the shank 4 using a suitable driving tool (not shown) that operably drives and rotates the shank body 6 by engagement thereof at the internal drive 150. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 151 by first threading the wire into the opening at the bottom 128 and then out of the top opening at the drive feature 150. The shank 4 is then driven into the vertebra using the wire as a placement guide. It is foreseen that the shank and other bone screw assembly parts, the rod 21 (also having a central lumen in some embodiments) and the closure top 18 having the central bore 62 can be inserted in a percutaneous or minimally invasive surgical manner, utilizing guide wires. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

With further reference to FIG. 42, the pre-assembled receiver, insert and retainer are placed above the shank upper portion 8 until the shank upper portion is received within the opening 207. With particular reference to FIGS. 43-45, as the shank upper portion 8 is moved into the interior 161 of the receiver base, the shank upper portion 8 presses upwardly against the retainer 12 in the recess partially defined by the spherical surface 202. As the portion 8 continues to move upwardly toward the channel 162, the shank surface 144 forces outward movement of the retainer 12 towards the surface 202 in the receiver expansion chamber or area as the shank 4 presses the retainer 12 up against the receiver annular ledge surface or ceiling 199. The retainer 12 initially expands about the shank upper spherical surface 144 and then slides along the cylindrical surface 142, and finally snapping or popping into the recessed cylindrical surface 138, the surface 225 of the retainer 12 fully contacting and frictionally engaging the cylindrical surface 138 between the shank lower ledge 136 and the upper ledge 140. At this time, the retainer 12 is in a neutral or slightly expanded state, fully snapped onto the shank upper portion 8 with both the retainer 12 and shank upper portion 8 in pivotal relation with the receiver 10.

Figure 46:
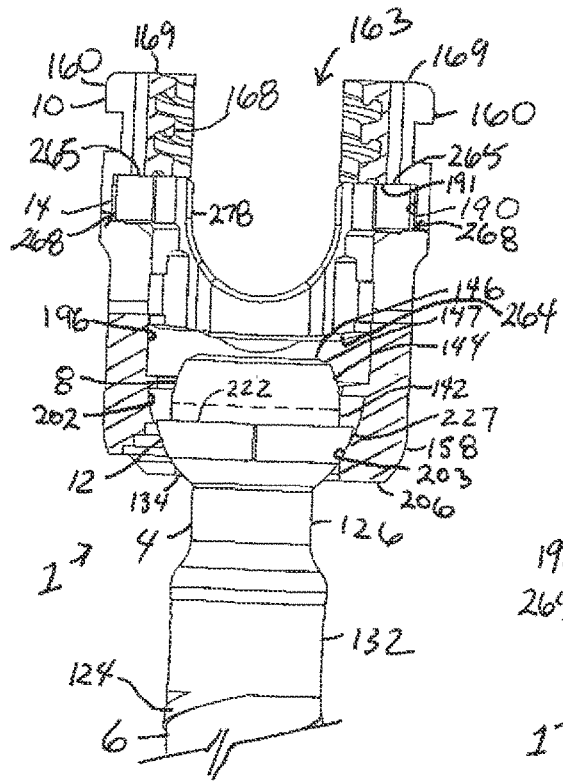
FIG. 46 is a partial front elevational view, similar to FIG. 45, with portions broken away to show the detail thereof and showing the retainer dropped down to a seated position within the receiver.
Figure 47:
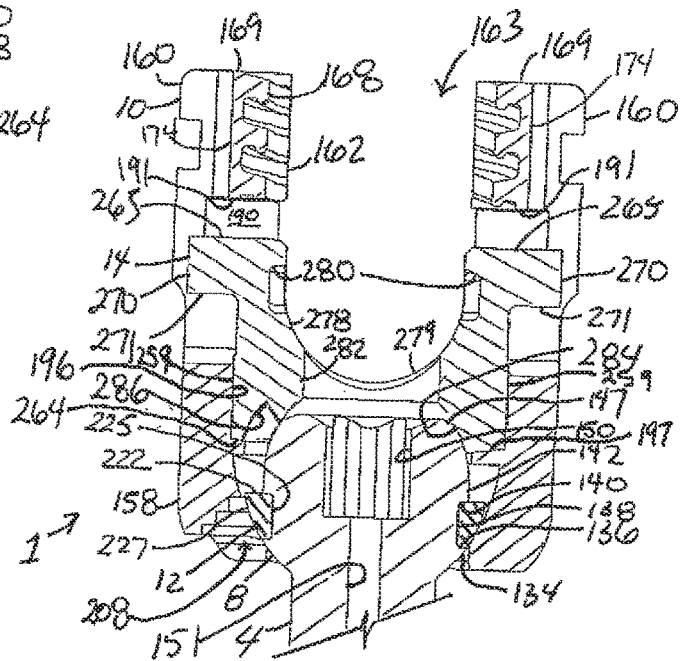
FIG. 47 is an enlarged and partial front elevational view with portions broken away, similar to FIG. 46 and further showing the insert after being pressed downwardly into friction fit engagement with the shank.
Figure 48:
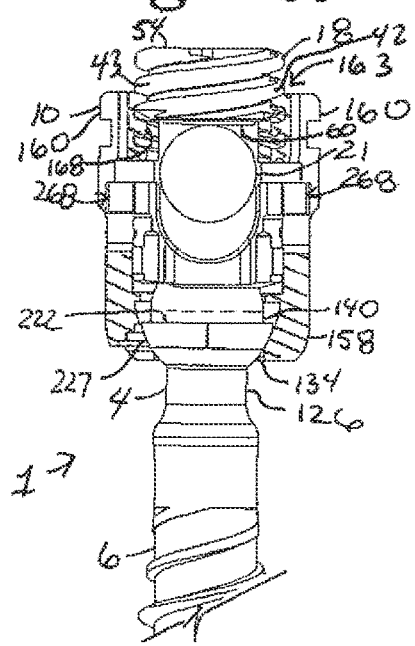
FIG. 48 is an enlarged and partial front elevational view with portions broken away of the assembly of FIG. 18, shown with the closure top partially assembled as also shown in FIG. 3.

With reference to FIG. 46, the shank 4 and attached retainer 12 are then moved downwardly into a desired position with the retainer seated on the surface 203. With reference to FIG. 47, the insert 14 may be pressed downwardly by a tool (not shown) entering at the receiver grooves 174, for example, and pressing down on the insert wings 268, to result in a frictional engagement between the insert inner spherical surface 284 and the shank upper domed surface 144 to an extent that the shank is pivotable with respect to the receiver, but in a non-floppy manner. The insert 14 remains in such position due to interference fit engagement between the insert outer band surfaces 259 and the receiver cylindrical surfaces 196. Alternatively, the insert 14 may be pushed into such interference fit by a rod 21 and closure top 18. Typically, tools are first used to provide the non-floppy arrangement between the insert 14 and the shank head 8, followed by performing a locking engagement utilizing the rod 21 and closure top 18 as shown in FIG. 48. In some embodiments, when the receiver 10 is pre-assembled with the shank 4, the entire assembly 1 may be implanted after the insert 14 is pressed into non-floppy frictional engagement with the shank head 8 by inserting the driving tool (not shown) into the receiver and the shank drive 150 and rotating and driving the shank 4 into a desired location of the vertebra 17.

Figure 49:
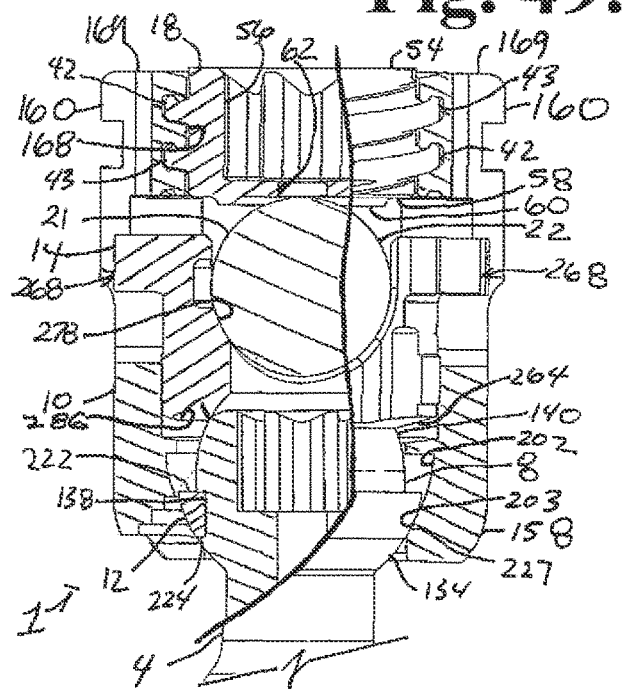
FIG. 49 is an enlarged and partial front elevational view with portions broken away, similar to FIG. 48 and further showing the closure fully assembled between arms of the receiver.

Again, with reference to FIG. 48 and also FIG. 49, the rod 21 is eventually positioned in an open or percutaneous manner in cooperation with the at least two bone screw assemblies 1. The closure structure 18 is then inserted into and advanced between the arms 160 of each of the receivers 10. The closure structure 18 is rotated, using a tool engaged with the inner drive 56 until a selected pressure is reached at which point the rod 21 engages the U-shaped seating surface 278 of the compression insert 14, further pressing the insert spherical surface 284 against the shank spherical surface 144, pressing the shank upper portion 8 and attached retainer 12 into locked frictional engagement with the receiver 10. With specific reference to FIGS. 3, 48, and 49, as the multi-start closure structure 18 rotates and moves downwardly into the respective receiver 10, the rim 60 engages and penetrates the rod surface 22, the closure structure 18 pressing downwardly against and biasing the rod 21 into compressive engagement with the insert 14 that urges the shank upper portion 8 and attached retainer 12 into locking engagement with the receiver, the retainer 12 spherical surface 227 frictionally abutting the spherical seating surface 203 of the receiver 10. For example, about 80 to about 120 inch pounds of torque on the closure top may be applied for fixing the bone screw shank 6 with respect to the receiver 10. Also, for example, with reference to FIGS. 52-58, when the shank 4 is disposed at an angle with respect to the receiver 10, the lower spherical surface 134 of the shank upper portion 8 may also be in frictional engagement with a portion of the receiver spherical seating surface 203. The retainer 12 may also expand slightly upon locking, providing a full and secure frictional locking engagement with the receiver at the surface 203.

If removal of the rod 21 from any of the bone screw assemblies 1 is necessary, or if it is desired to release the rod 21 at a particular location, disassembly is accomplished by using the driving tool (not shown) that mates with the internal drive 56 on the closure structure 18 to rotate and remove such closure structure from the cooperating receiver 10. Disassembly is then accomplished in reverse order to the procedure described previously herein for assembly.

With further reference to FIG. 49 and also with reference to FIG. 50, at this time, the closure top 18 may be loosened or removed and/or the rod 21 may be adjusted and/or removed and the frictional engagement between the insert 14 and the receiver 10 at the receiver surface 196 will remain locked in place, advantageously maintaining a locked angular position of the shank 4 with respect to the receiver 10. Thus, at this time, another rod, such as the deformable rod 21' and cooperating alternative multi-start closure top 18' may be loaded onto the already locked-up assembly to result in an alternative assembly. It is noted that the closure drive 56' may advantageously be made smaller than the drive of the closure 18, such that the deformable rod 21' is not unduly pressed or deformed during assembly since the polyaxial mechanism is already locked.

Figure 51:
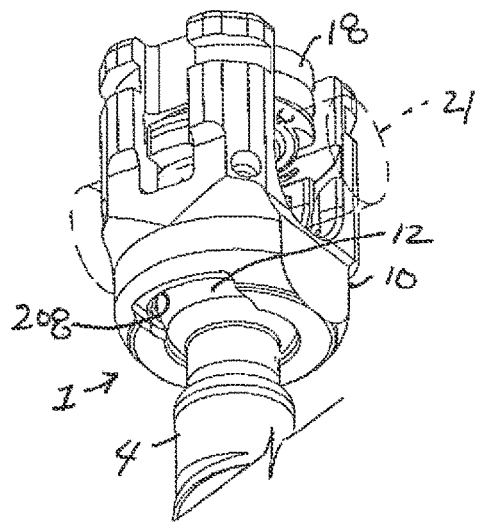
FIG. 51 is a reduced and partial perspective view of the assembly of FIG. 49.
Figure 52:
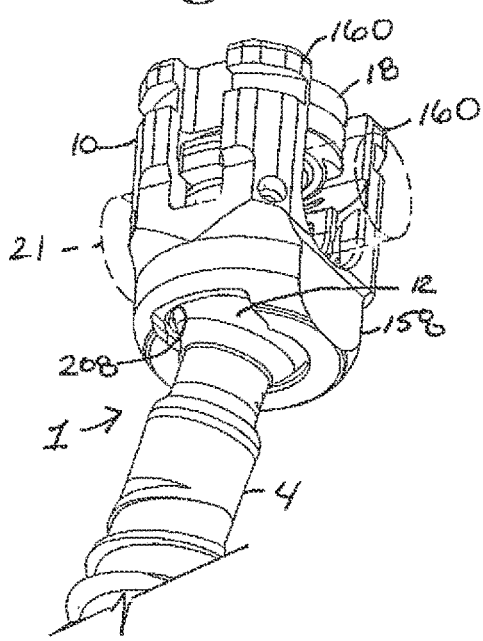
FIG. 52 is a partial perspective view, similar to FIG. 51, but showing the shank disposed at an eighteen degree angle (cephalic) with respect to the receiver.
Figure 53:
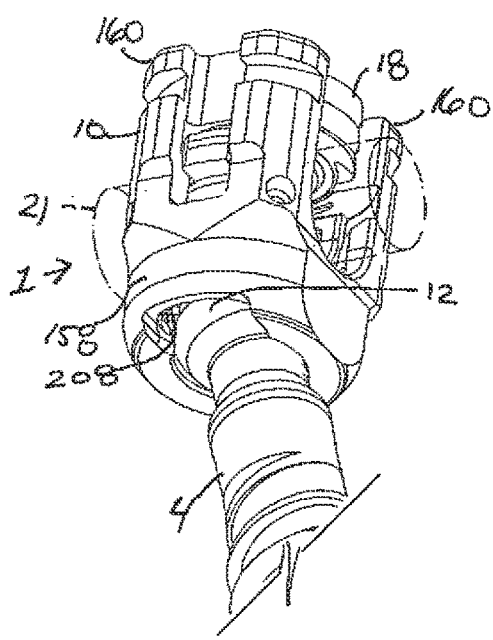
FIG. 53 is a partial perspective view, similar to FIG. 52, but showing the shank disposed at an eighteen degree angle (caudal) with respect to the receiver.
Figure 54:
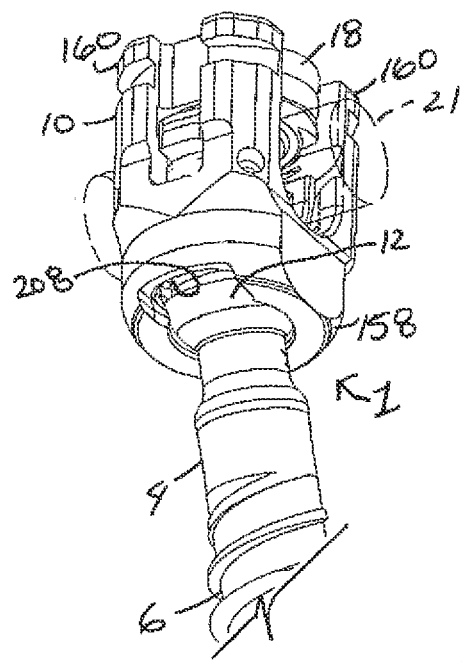
FIG. 54 is a partial perspective view, similar to FIG. 53, but showing the shank disposed at an eighteen degree angle (lateral) with respect to the receiver.
Figure 55:
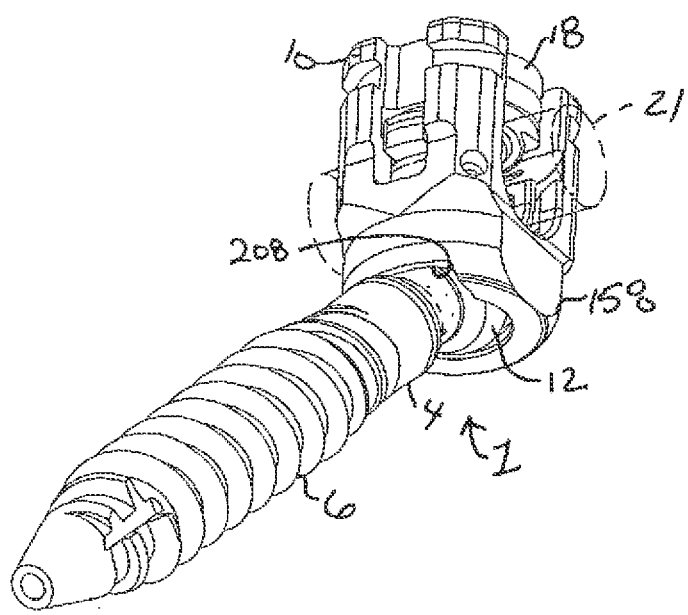
FIG. 55 is a partial perspective view, similar to FIG. 54, but showing the shank disposed at a forty-two degree (medial) by eight degree (cephalic) angle with respect to the receiver.
Figure 56:
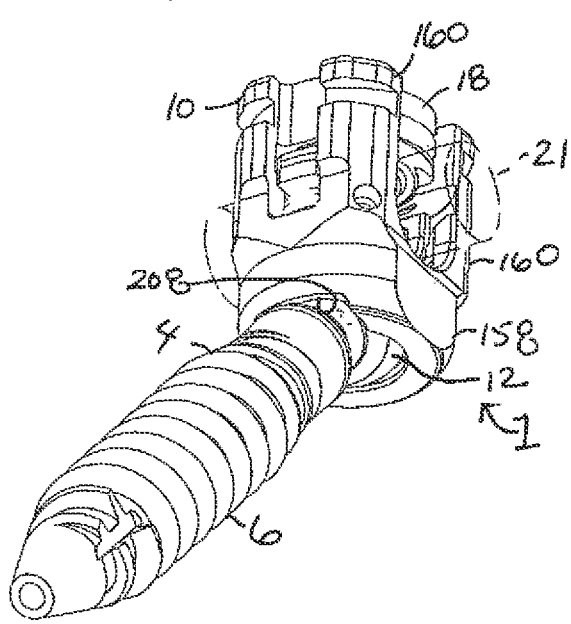
FIG. 56 is a partial perspective view, similar to FIG. 55, but showing the shank disposed at a forty-two degree (medial) angle with respect to the receiver.
Figure 57:
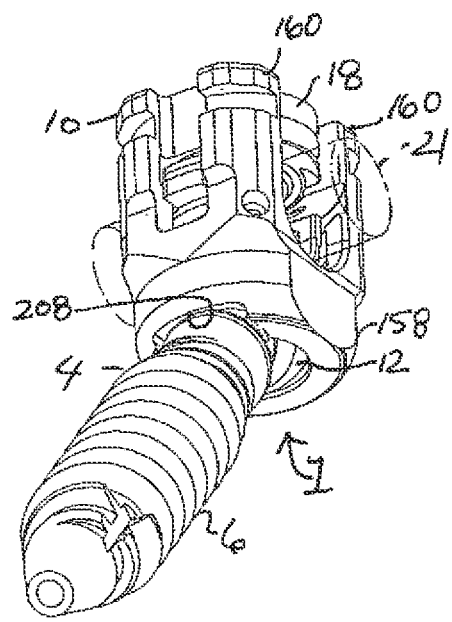
FIG. 57 is a partial perspective view, similar to FIG. 56, but showing the shank disposed at a forty-two degree (medial) by eight degree (caudal) angle with respect to the receiver.

With reference to FIGS. 51-58, prior to locking the insert 14 against the shank head 8, the shank 4 may be pivoted to a plurality of potentially desirable positions with respect to the receiver 10, followed by locking of the polyaxial mechanism by fully mating the multi-start closure top 18 with the receiver 10. For example, different angular or articulated positions of the shank 4 with respect to the receiver 10 are shown, some making full use of the stepped cut-out 208 and the c-shaped groove forming the surface 200 of the receiver and/or the notch 286 of the insert 14. For reference, FIG. 51 illustrates a zero degree relationship between the shank 4 and the receiver 10. In other words, the axis A of the shank is aligned with the axis B of the receiver. FIG. 52 shows the shank 4 pivoted laterally of the receiver cut-out portion 208 in an eighteen degree cephalic relationship. FIG. 53 shows the shank 4 pivoted away from the receiver cut-out portion 208 in an eighteen degree caudal relationship. FIG. 54 illustrates the shank 4 being pivoted with respect to the receiver 10 at an eighteen degree lateral relationship. FIG. 55 shows the shank 4 pivoted toward the receiver cut-out portion 208 at a forty-two degree medial by eight degree cephalic relationship. FIG. 56 shows the shank 4 pivoted toward the receiver cut-out portion 208 at a forty-two degree medial relationship. FIGS. 57 and 58 show the shank 4 pivoted toward the receiver cut-out portion 208 at a forty-two degree medial by eight degree caudal relationship. FIG. 58 also shows that in such a pivoted relationship between the shank 4 and the receiver 10, a portion of the retainer 12 moves past the receiver surface 200 and is received by the notch 286 in the insert 14.

Figure 9:
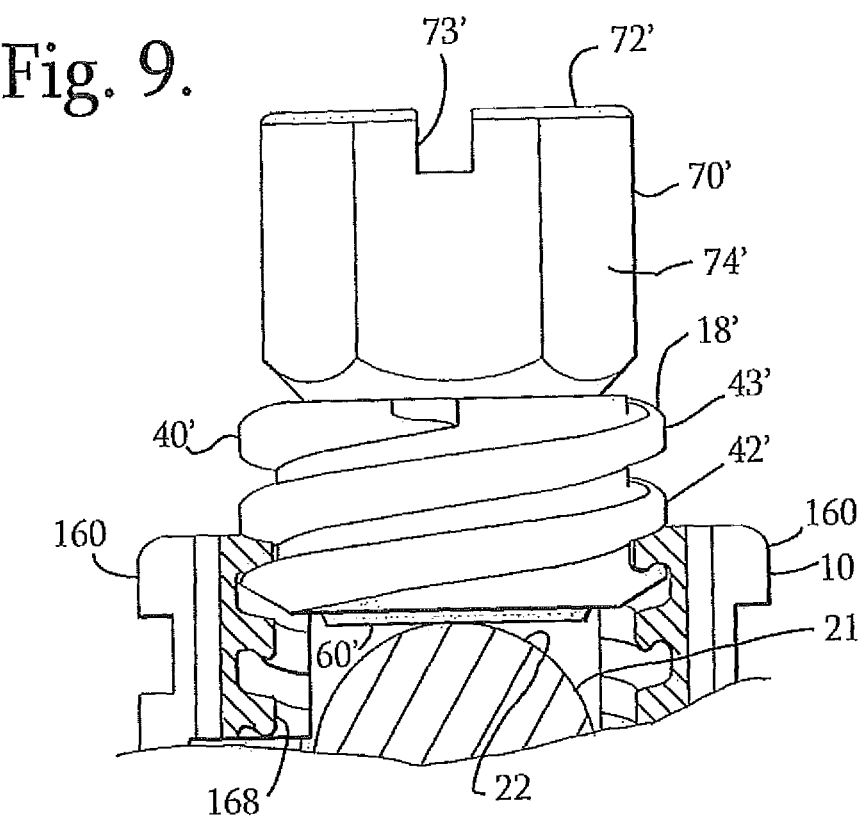
FIG. 9 is a front elevational view of an alternative closure of an embodiment of the invention, similar to the closure of FIG. 1, but including a break-off head, the alternative closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.
Figure 10:
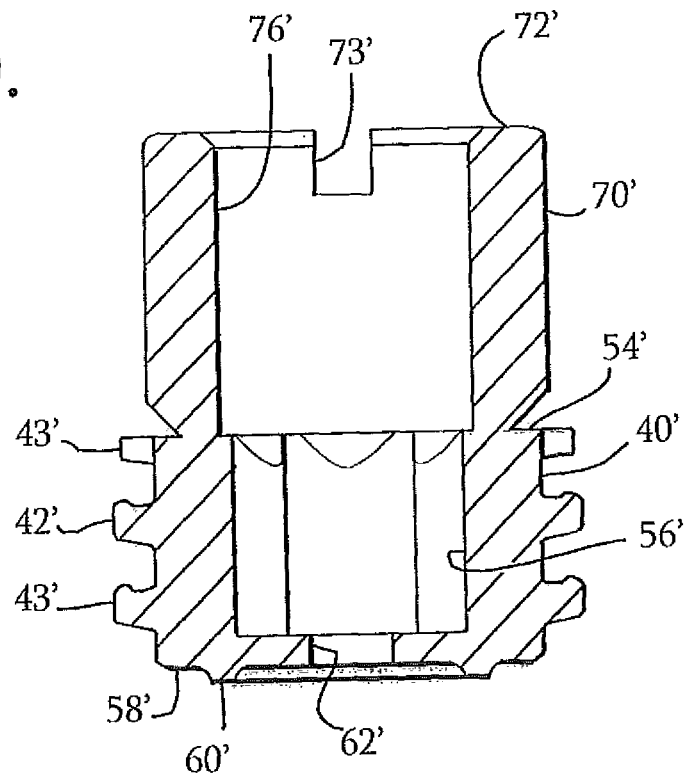
FIG. 10 is another front elevational view of the closure of FIG. 9 with portions broken away to show the detail thereof.

With reference to FIGS. 9 and 10, an alternative closure top 18' is shown that is almost identical to the closure top 18. However, the top 18' differs from the top 18 in that the top 18' includes a break-off head 70' that further includes a top surface 72' having tooling notches 73', an outer faceted driving surface 74', illustrated as having a hex-shaped profile, and an inner bore 76'. Otherwise, the closure top 18' includes a body 40', a first helical form 42', a second helical form 43', a body top surface 54', a body internal drive 56', a base 58', a rim 60', a cannulation bore 62' and a drive base surface 63' that is the same or substantially similar to the respective body 40, first helical form 42, second helical form 43, body top surface 54, internal drive 56, base 58, rim 60, cannulation bore 62 and drive base surface 63 previously described herein with respect to the closure top 18. The break-off head 70' is integral with the body 40' at the body top surface 54'. The inner bore 76' communicates with the inner drive 56' and the cannulation bore 62'. The break-off head 70' is designed to allow such head 70' to break from the body 40' at or near the top surface 54' at a preselected torque, for example, 70 to 140 inch pounds, when a hex-shaped tool (not shown) engages the outer surfaces 74' and drives the closure structure 18' into the receiver 10 as shown in FIG. 9. The inner drive 56' is used for disassembly or loosening of the closure 18' from the receiver 10, and re-tightening, if needed.

Figure 11:
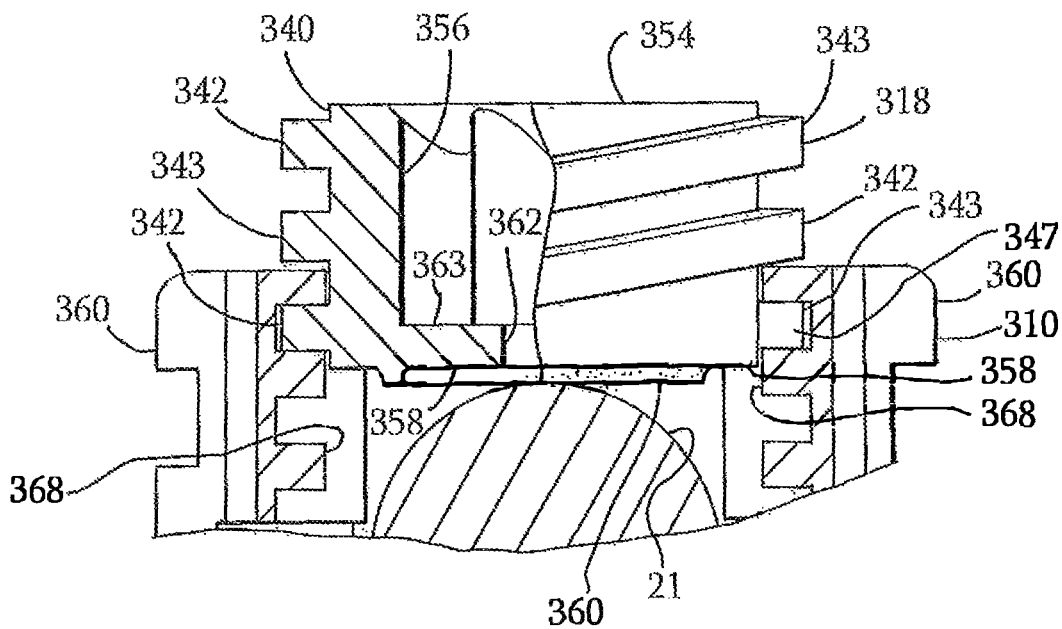
FIG. 11 is a front elevational view of an alternative square-thread closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 11, another alternative multi-start closure top 318 is shown that is almost identical to the closure top 18 with the exception that the two flange forms 42 and 43 with respective starts 46 and 47 have been replaced with square threads 342 and 343 with respective starts 346 (not shown) and 347. Otherwise, the dual or double start closure top 318 includes a body 340, a body top surface 354, a body internal drive 356, a base 358, a rim 360', a cannulation bore 362 and a drive base surface 363 that is the same or substantially similar to the respective body 40, body top surface 54, internal drive 56, base 58, rim 60, cannulation bore 62 and drive base surface 63 previously described herein with respect to the closure top 18. In FIG. 11, the closure top 318 is shown partially wound into a polyaxial bone screw receiver 310 having opposed arms 360 with inner surfaces equipped with guide and advancement structures 368 that are sized and shaped to simultaneously closely receive and mate with the square threads 342 and 343 of the double closure structure 318. Otherwise, the receiver 310 is identical or substantially similar to the receiver 10.

Figure 12:
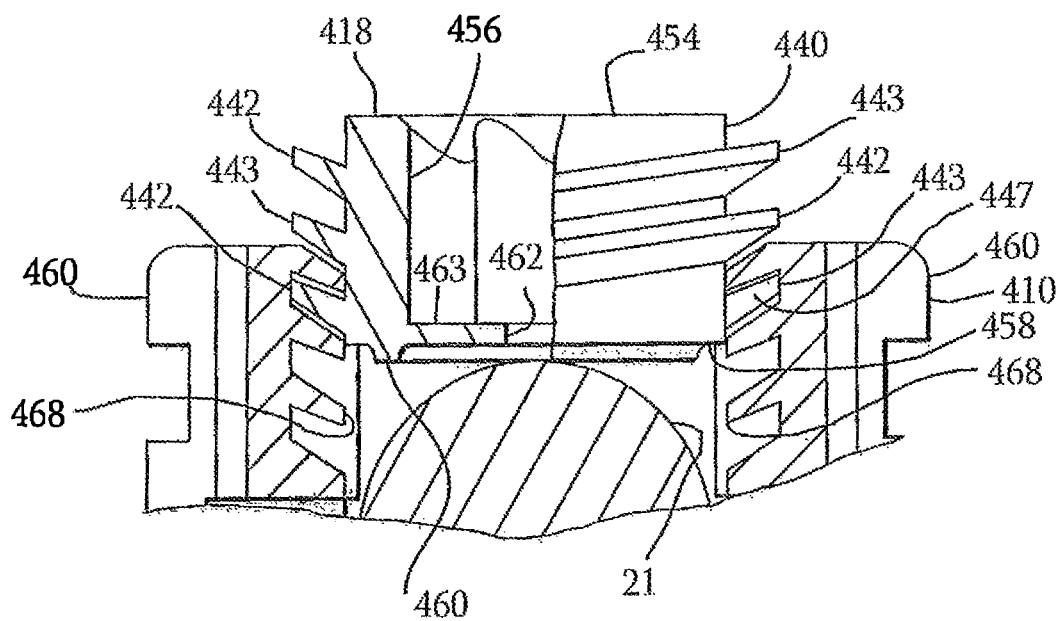
FIG. 12 is a front elevational view of an alternative reverse angle closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 12, an alternative multi-start closure top 418 is shown that is almost identical to the closure top 18 with the exception that the two flange forms 42 and 43 with respective starts 46 and 47 have been replaced with reverse angle threads 442 and 443 with respective starts 446 (not shown) and 447. Otherwise, the dual or double start closure top 418 includes a body 440, a body top surface 454, a body internal drive 456, a base 458, a rim 460', a cannulation bore 462 and a drive base surface 463 that is the same or substantially similar to the respective body 40, body top surface 54, internal drive 56, base 58, rim 60, cannulation bore 62 and drive base surface 63 previously described herein with respect to the closure top 18. The closure top 418 is shown partially wound into a polyaxial bone screw receiver 410 having opposed arms 460 with inner surfaces equipped with guide and advancement structures 468 that are sized and shaped to simultaneously closely receive and mate with the reverse angle threads 442 and 443 of the double start closure structure 418. Otherwise, the receiver 410 is identical or substantially similar to the receiver 10.

Figure 13:
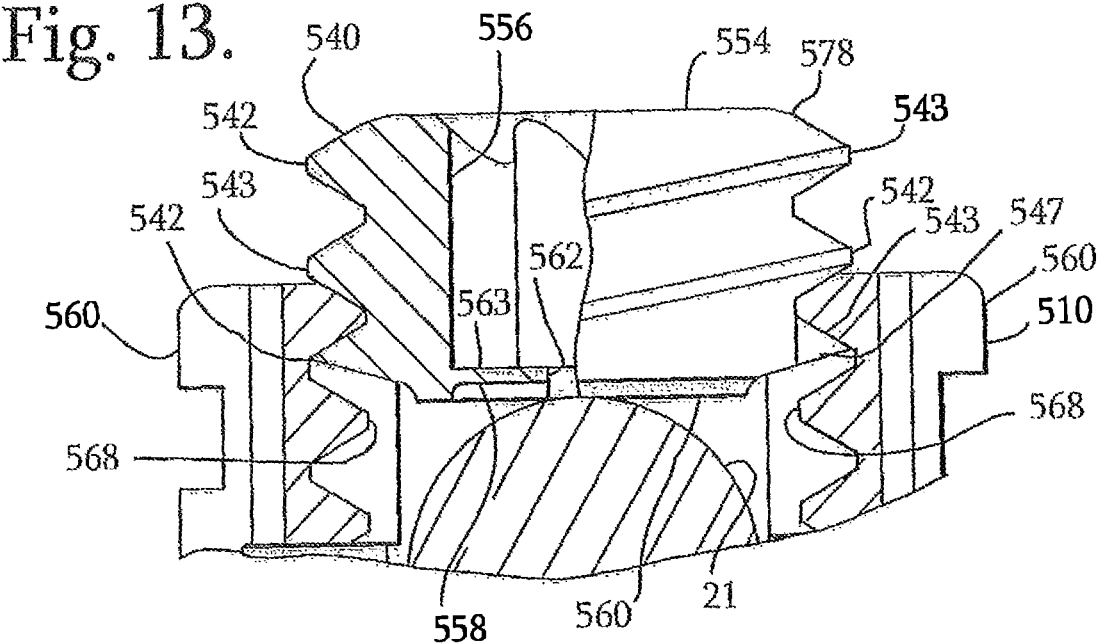
FIG. 13 is a front elevational view of an alternative v-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 13, another alternative multi-start closure top 518 is shown that is almost identical to the closure top 18 with the exception that the two flange forms 42 and 43 with respective starts 46 and 47 have been replaced with v-threads 542 and 543 with respective starts 546 (not shown) and 547. Otherwise, the dual or double start closure top 518 includes a body 540, a body top surface 554, a body internal drive 556, a base 558, a rim 560', a cannulation bore 562 and a drive base surface 563 that is the same or substantially similar to the respective body 40, body top surface 54, internal drive 56, base 58, rim 60, cannulation bore 62 and drive base surface 63 previously described herein with respect to the closure top 18. The closure top 518 is shown partially wound into a polyaxial bone screw receiver 510 having opposed arms 560 with inner surfaces equipped with guide and advancement structures 568 that are sized and shaped to simultaneously closely receive and mate with the threads 542 and 543 of the double start closure structure 518. Otherwise, the receiver 510 is identical or substantially similar to the receiver 10.

Figure 14:
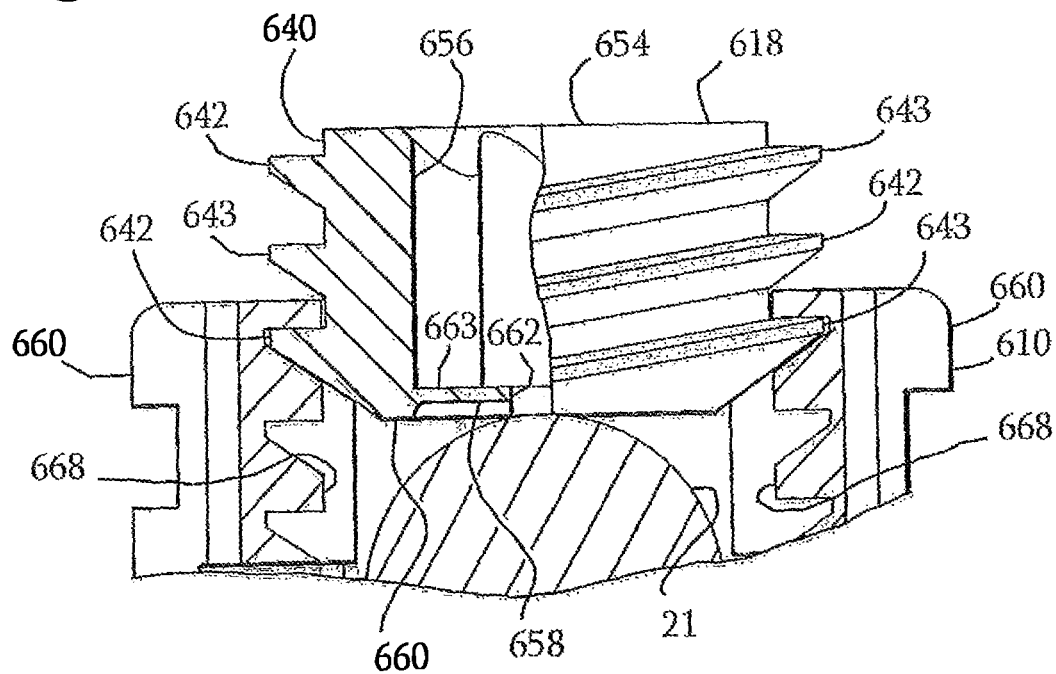
FIG. 14 is a front elevational view of an alternative buttress-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 14, another alternative multi-start closure top 618 is shown that is almost identical to the closure top 18 with the exception that the two flange forms 42 and 43 with respective starts 46 and 47 have been replaced with buttress threads 642 and 643 with respective starts 446 and 447 (not shown). Otherwise, the dual or double start closure top 618 includes a body 640, a body top surface 654, a body internal drive 656, a base 658, a rim 660', a cannulation bore 662 and a drive base surface 663 that is the same or substantially similar to the respective body 40, body top surface 54, internal drive 56, base 58, rim 60, cannulation bore 62 and drive base surface 63 previously described herein with respect to the closure top 18. The closure top 618 is shown partially wound into a polyaxial bone screw receiver 610 having opposed arms 660 with inner surfaces equipped with guide and advancement structures 668 that are sized and shaped to simultaneously closely receive and mate with the buttress threads 642 and 643 of the double start closure structure 618. Otherwise, the receiver 610 is identical or substantially similar to the receiver 10.

Figure 15:
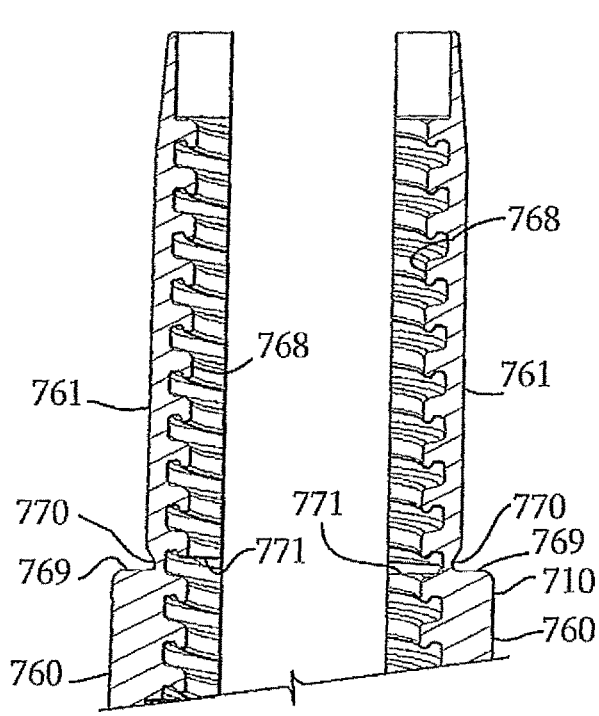
FIG. 15 is a partial front elevational view of an embodiment of a multi-start open bone anchor receiver of an embodiment of the invention with portions broken away to show the detail thereof, the receiver including break-off tabs.
Figure 16:
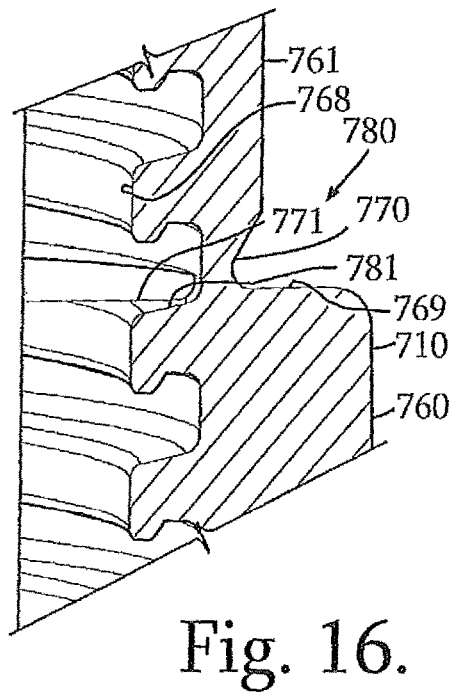
FIG. 16 is an enlarged and partial front elevational view of the receiver of FIG. 15 with portions broken away to show the detail thereof.

With reference to FIGS. 15 and 16, an open receiver 710 is illustrated that is substantially similar to the receiver 10 previously described herein with the exception that the receiver 710 includes opposed arms 760, each having an integral upstanding break-off extension 761. Each receiver arm 760 and integral extension 761 has an inner helically wound guide and advancement structure 768 that is sized and shaped to mate with the flange forms 42 and 43 of the dual start closure 18 previously described herein. The break-off extensions 761 are initially integral with the respective arms 760 and are then broken off by a user after the closure 18 has been rotatingly advanced along the arm extensions 761 and into the channel located between the receiver arms 760. In the illustrated embodiment, in addition to an outer groove or notch 770 located at or near a top surface 769 of each of the arms 760 where the extensions 761 break off from the receiver arms, illustrated inner arm surfaces include a recess or cut 771, best shown in FIG. 16, that runs substantially horizontally. Each recess 771 is curved and elongate and disposed somewhat cross-wise or transverse to the respective flange form 768. For example, with reference to the arm 760 shown in FIG. 16, the recess 771 cuts into a weakened region, generally 780, where the arm 760 joins with the respective attached adjacent extension 761, the curved and elongate recess 771 beginning at a lower portion or location 781 of the flange form recess or segment and terminating at an opposed upper end location of the flange form segment, while otherwise leaving the flange form 768 intact. Stated in another way, the substantially horizontally extending recess 771 cuts into both a lead portion and a trailing portion of each of the flange form segments located near and directly above the opposed arms 760 and substantially opposite the notch 770, thus further weakening the region where the extension and the arm attach, without destroying the flange form path, so that the closure 18 is not derailed by the recess 771 or otherwise prohibited from moving downwardly into the receiver channel formed between the receiver arms 760.

Figure 17:
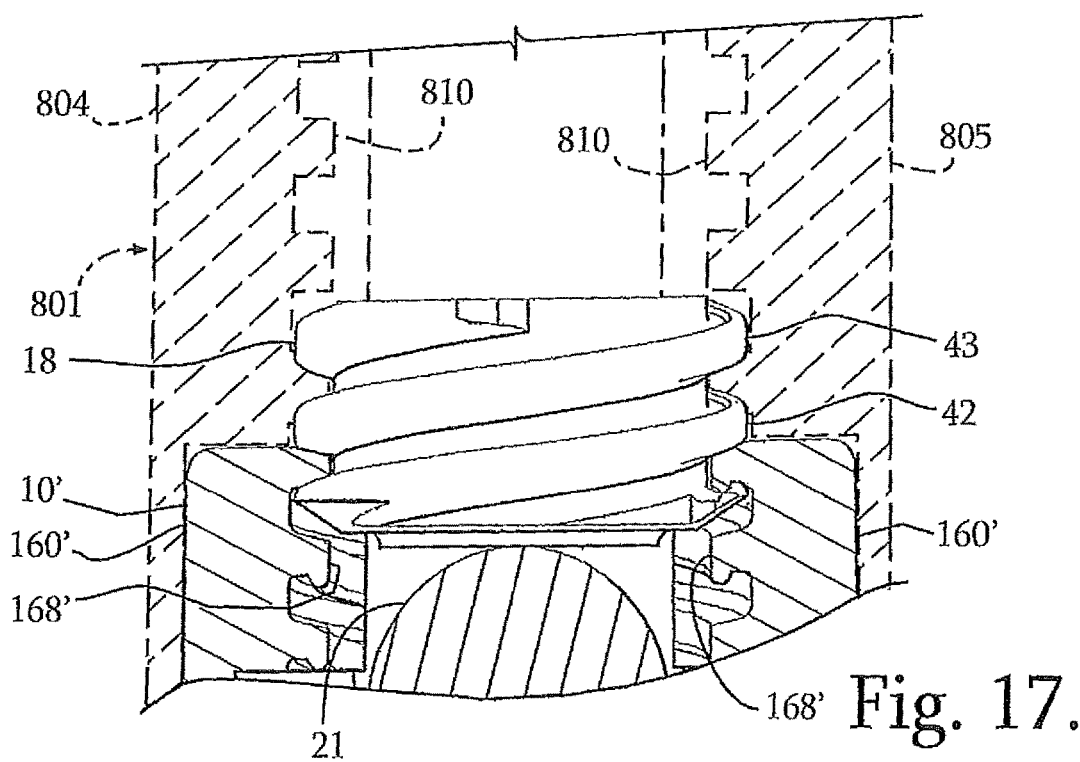
FIG. 17 is a partial front elevational view of an embodiment of a bone anchor receiver having a guide and advancement structure that matingly cooperates with the multi-start closure of FIG. 1, also shown in front elevation, the receiver having portions broken away to show the detail thereof, and further shown with a guide tool, shown in phantom, the guide tool having a multi-start guide and advancement structure receiving inner surface synchronized with the bone anchor receiver guide and advancement structure.
Figure 21:
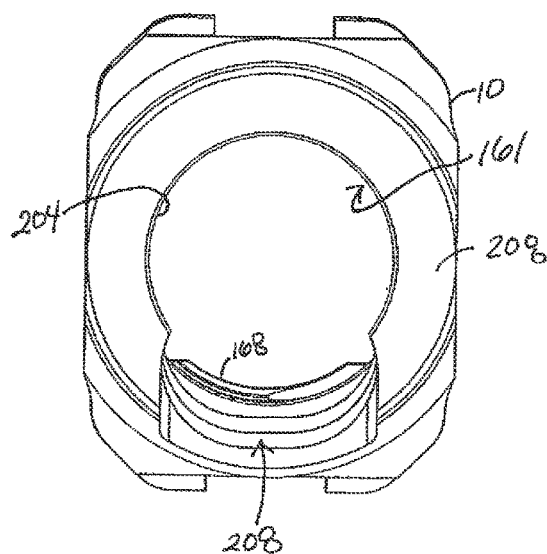
FIG. 21 is a bottom plan view of the receiver of FIG. 19.
Figure 22:
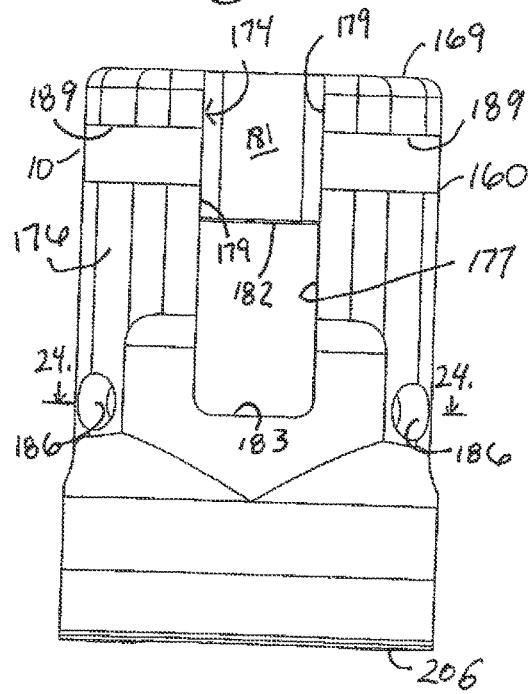
FIG. 22 is a side elevational view of the receiver of FIG. 19.

With reference to FIG. 17, the multi-start closure 18 is shown cooperating with a spinal implant receiver, such as a bone screw receiver 10' and a discrete, detachable guide tool 801. The elongate guide tool 801, only partially shown in FIG. 17, is typically sized for extending from the bone screw receiver 10' upwardly to a location outside of a patient, the tool providing a guide channel for operably guiding the rod 21 or other longitudinal connecting member from a position exterior of the bone screw receiver 10' toward and into the bone screw receiver 10'. The illustrated guide tool has opposed arms 805, each arm having a helical guide and advancement structure 810 thereon that is illustrated as a square thread form, but may be of other geometry, including a flange form the same or similar to the flange forms 168' of the receiver 10' that mates with the flange forms 42 and 43 of the closure structure 18. Thus, the illustrated structures 810 are sized and shaped for receiving and rotating engagement with a dual start closure. The closure 18 is shown partially wound into the receiver 10' that is identical or substantially similar to the receiver 10 with the exception of certain outer arm surface features (not shown). Thus, the receiver 10' includes opposed arms 160' with inner surfaces having guide and advancement structures 168' that are sized and shaped to simultaneously closely receive and mate with the flange forms 42 and 43 of the dual start closure structure 18. The guide tool 801 includes attachment structure for detachable attachment to the receiver 10' (not shown), that may take a variety of forms and methods, including, but not limited to a slide-on, slide-off attachment, a snap-on, rotate off attachment, a rotate-on and rotate-off attachment, to name a few. For example, cooperating attachment structure for both the tool and the receiver may be used that is disclosed in U.S. Pat. No. 7,470,279 and incorporated by reference herein. Returning to the inner helically wound guide and advancement structure 810 formed on each arm 804 of the guide tool 801, the structure 810 is sized and shaped for being aligned with the receiver arms 160' during removable attachment of the tool 801 with the respective bone screw receiver 10' so as to continue the helical pathway for the closure 18, the structures 810 being synchronized with the flange forms 168' to allow for the rotation and driving transfer of the closure 18 from the tool 801 into the receiver 10'.

It is to be understood that while certain forms of the present invention have been illustrated and described herein, it is not to be limited to the specific forms or arrangement of parts described and shown.

What is claimed is:

1. A medical implant assembly for securing an elongate rod to a bone anchor, the medical implant assembly comprising:
    a receiver comprising a central axis, a base portion, an upper portion defining a channel configured to receive the elongate rod, a front face, a back face opposite the front face, and a top surface, the channel extending between the front face and the back face of the receiver and extending to the top surface defining a top of the receiver, the receiver further comprising an interior surface and an exterior surface opposite the interior surface, the interior surface having a helically wound receiver thread formed therein, the exterior surface having first and second horizontal curvate extending instrument engaging grooves (HCEIEG) formed therein and being proximate the top surface of the receiver, each of the front face and back face including a planar surface extending parallel with respect to each other and the central axis, and the exterior surface including first and second outward-facing planar surfaces extending parallel with respect to each other and being positioned below the first and second HCEIEG, respectively, the first HCEIEG including a first outer end opening onto the planar surface on the front face of the receiver, the second HCEIEG including a second outer end opening onto the planar surface on the back face of the receiver; and
    a threaded plug configured to be positioned within the channel to secure the elongate rod to the receiver in a locked configuration, the threaded plug comprising a cylindrical body, a longitudinal axis, a first outer diameter, a planar top surface including a central internal drive structure with a tool abutment surface defined therein, a through-bore centered around the longitudinal axis and extending below the tool abutment surface, a lower surface including a protrusion centrally positioned around the longitudinal axis and having a second outer diameter that is less than the first outer diameter, an external side surface on the cylindrical body having a continuous helically wound closure thread configured to rotatably mate with the helically wound receiver thread, the continuous helically wound closure thread including a lower leading surface, an upper trailing surface opposite the lower leading surface, and a cylindrical outer crest surface positioned between the upper trailing surface and the lower leading surface, the cylindrical outer crest surface extending parallel to the longitudinal axis, and the lower leading surface and the upper trailing surface both extending perpendicular to the longitudinal axis,
    wherein, when the medical implant assembly is in a locked configuration via the threaded plug: the protrusion on the threaded plug is configured to engage the elongate rod positioned in the channel of the receiver; and the threaded plug does not extend overtop of any portion of the top surface defining the top of the receiver.

2. The medical implant assembly of claim 1, wherein the lower surface on the protrusion includes an annular outer edge.

3. The medical implant assembly of claim 1, wherein the protrusion includes a lower circumferential recess in communication with the through-bore.

4. The medical implant assembly of claim 1, wherein the receiver includes breakoff extensions with internal helically wound threads.

5. The medical implant assembly of claim 1, wherein the receiver includes a lower pressure insert having a rod-receiving channel with upright arms that flare outwardly near an upper end thereof and a lower end configured to engage a head of the bone anchor positionable in the base portion of the receiver when in the locked configuration.

6. A method of securing an elongate rod to a bone anchor using a medical implant assembly, the method further comprising:
    providing the medical implant assembly of claim 1; and
    positioning the threaded plug within the channel of the upper portion of the receiver, at least a portion of the bone anchor positioned within the receiver; and
    advancing the threaded plug within the channel of the upper portion of the receiver to secure the elongate rod to the receiver in the locked configuration.

7. A medical implant assembly for securing an elongate rod to a bone anchor, the medical implant assembly comprising:
    a receiver having an upper portion with an inner surface at least partially configured as a helically wound thread extending up to a top surface of the receiver, and a channel formed in the upper portion of the receiver and configured to receive the elongate rod; and
    a plug being threaded and configured to be positioned within the upper portion, the plug having an axis of rotation, a continuously helically wound thread form, and a bottom surface with an annular outer edge, the bottom surface configured to engage the elongate rod, the continuously helically wound thread form having a start structure with an upper surface extending between a root and a crest of the continuously helically wound thread form, the start structure having a leading face extending below the upper surface to a lower beveled surface of the start structure extending up to the leading face, the leading face including a partial concave surface adjacent the root and a partial convex surface adjacent the crest, the partial concave and partial convex surfaces each defined by a radius of curvature that is substantially equal with respect to each other and less than a radius of curvature for the crest, the lower beveled surface of the start structure adjacent, above and spaced apart from the annular outer edge of the bottom surface so as to not be connected with the annular outer edge thereof, the bottom surface being on a centralized lower extending portion of the plug spaced below the lower beveled surface of the starting structure.

8. The medical implant assembly of claim 7, wherein the partial concave surface blends with the partial convex surface at a location that is substantially midway on the leading face between the root and the crest of the continuously helically wound thread form.

9. The medical implant assembly of claim 8, wherein at least a partial planar surface portion is located substantially midway on the leading face of the start structure so as to tangentially blend the partial concave surface with the partial concave convex surface therebetween.

10. The medical implant assembly of claim 7, wherein the start structure is a first start structure disposed at a diametrically opposite on the plug from a second start structure so as to have the first start structure and the second start structure positioned 180 degrees apart from each other.

* * * * *